United States Patent
Peyman

(10) Patent No.: US 9,510,974 B1
(45) Date of Patent: *Dec. 6, 2016

(54) LASER COAGULATION OF AN EYE STRUCTURE OR A BODY SURFACE FROM A REMOTE LOCATION

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 43 days.

This patent is subject to a terminal disclaimer.

(21) Appl. No.: 14/715,325

(22) Filed: May 18, 2015

Related U.S. Application Data

(63) Continuation-in-part of application No. 13/865,901, filed on Apr. 18, 2013, now Pat. No. 9,037,217, which is a continuation-in-part of application No. 13/573,100, filed on Aug. 20, 2012, now Pat. No. 8,903,468, which is a continuation-in-part of application No. 12/925,518, filed on Oct. 22, 2010, now Pat. No. 8,452,372.

(60) Provisional application No. 61/455,111, filed on Oct. 13, 2010.

(51) Int. Cl.
*A61B 5/00* (2006.01)
*A61F 9/008* (2006.01)

(52) U.S. Cl.
CPC .. *A61F 9/00821* (2013.01); *A61F 2009/00844* (2013.01); *A61F 2009/00878* (2013.01); *A61F 2009/00897* (2013.01)

(58) Field of Classification Search
USPC ........................................ 600/407, 473, 476
See application file for complete search history.

(56) References Cited

U.S. PATENT DOCUMENTS

| | | |
|---|---|---|
| 4,213,678 A | 7/1980 | Pomerantzeff et al. |
| 4,247,176 A | 1/1981 | Ito |
| 4,736,744 A | 4/1988 | Koike et al. |
| 4,759,360 A | 7/1988 | Nakanishi et al. |
| 4,838,680 A | 6/1989 | Nunokawa |
| 5,049,147 A | 9/1991 | Danon |
| 5,572,266 A | 11/1996 | Ohtsuka |
| 5,713,047 A | 1/1998 | Kohayakawa |
| 5,742,374 A | 4/1998 | Nanjo et al. |

(Continued)

FOREIGN PATENT DOCUMENTS

WO    WO2010/129074    * 11/2010

OTHER PUBLICATIONS

Konig et al. "Nanodissection of Human Chromosomes and Ultraprecise Eye Surgery With Nanojoule Near Infrared Femtosecond Laser Pulses." Proceedings of SPIE, vol. 4633, 2002, pp. 11-22.*

(Continued)

*Primary Examiner* — James Kish
(74) *Attorney, Agent, or Firm* — The Law Office of Patrick F. O'Reilly III, LLC

(57) ABSTRACT

An integral laser imaging and coagulation apparatus, and associated systems and methods that allow a physician (e.g., a surgeon) to perform laser surgical procedures on an eye structure or a body surface with an integral laser imaging and coagulation apparatus disposed at a first (i.e. local) location from a control system disposed at a second (i.e. remote) location, e.g., a physician's office. In some embodiments, communication between the integral laser imaging and coagulation apparatus and control system is achieved via the Internet®.

20 Claims, 12 Drawing Sheets

(56) References Cited

U.S. PATENT DOCUMENTS

| | | | |
|---|---|---|---|
| 5,815,242 | A | 9/1998 | Anderson et al. |
| 5,855,553 | A | 1/1999 | Tajima et al. |
| 5,923,399 | A | 7/1999 | Van de Velde |
| 5,943,116 | A | 8/1999 | Zeimer |
| 5,993,001 | A | 11/1999 | Bursell et al. |
| 6,173,068 | B1 | 1/2001 | Prokoski |
| 6,296,358 | B1 | 10/2001 | Cornsweet et al. |
| 6,529,617 | B1 | 3/2003 | Prokoski |
| 6,544,254 | B1 | 4/2003 | Bath |
| 6,546,198 | B2 | 4/2003 | Ohtsuka |
| 6,636,696 | B2 | 10/2003 | Saito |
| 7,079,688 | B1 | 7/2006 | Deco et al. |
| 7,206,435 | B2 | 4/2007 | Fujimura et al. |
| 7,206,626 | B2 | 4/2007 | Quaid, III |
| 8,070,289 | B2 | 12/2011 | Peyman |
| 8,121,663 | B2 | 2/2012 | Peyman et al. |
| 8,452,372 | B2 | 5/2013 | Peyman |
| 2003/0208189 | A1 | 11/2003 | Payman |
| 2006/0142657 | A1 | 6/2006 | Quaid et al. |
| 2007/0258626 | A1* | 11/2007 | Reiner .......................... 382/115 |
| 2009/0093798 | A1 | 4/2009 | Charles |
| 2009/0240149 | A1 | 9/2009 | Peyman |
| 2010/0060728 | A1 | 3/2010 | Bublitz et al. |
| 2010/0164950 | A1 | 7/2010 | Zhao et al. |
| 2010/0245766 | A1 | 9/2010 | Zhang et al. |
| 2012/0150159 | A1 | 6/2012 | Kunath-Fandrei et al. |

OTHER PUBLICATIONS

Csutak et al. "Agreement Between Image Grading of Conventional (45-degrees) and Ultra Wide-Angle (200-degrees) Digital Images of the Macula in the Reykjavik Eye Study." Eye, vol. 24. Published Jun. 4, 2010. pp. 1568-1575.*

Boyce et al. "Multispectral Iris Analysis: A Preliminary Study." Proceedings of Computer Vision and Pattern Recognition Workshop on Biometrics (CVPRW), Jun. 2006. pp. 1-9.*

Ertel et al., "Retinal Evaluation Efficacy of a Scanning Laser Opthalmoscope (Optos P200) Compared to a Digital Retinal Camera," White Rock Optometry Clinic, Nov. 4, 2009, pp. 1-15 (and p. 16 providing the earliest recorded date).

Office action on the merits (Non-Final Rejection) in U.S. Appl. No. 12/925,518, mailed on Mar. 7, 2012.

Second office action on the merits (Final Rejection) in U.S. Appl. No. 12/925,518, mailed on May 1, 2012.

Third office action on the merits (Non-Final Rejection) in U.S. Appl. No. 12/925,518, mailed on Dec. 5, 2012.

Fourth office action on the merits (Final Rejection) in U.S. Appl. No. 12/925,518, mailed on Mar. 21, 2013.

Notice of Allowance in U.S. Appl. No. 12/925,518, mailed on Apr. 12, 2013.

First action interview office action summary in U.S. Appl. No. 13/573,100, mailed on Apr. 2, 2014.

Second office action on the merits (Final Rejection) in U.S. Appl. No. 13/573,100, mailed on Jun. 16, 2014.

Notice of Allowance in U.S. Appl. No. 13/573,100, mailed on Sep. 30, 2014.

First office action on the merits (Non-Final Rejection) in U.S. Appl. No. 13/865,901, mailed on Mar. 20, 2014.

Second office action on the merits (Final Rejection) in U.S. Appl. No. 13/865,901, mailed on Aug. 15, 2014.

Notice of Allowance in U.S. Appl. No. 13/865,901, mailed on Jan. 21, 2015.

\* cited by examiner

LASER COAGULATION OF AN EYE STRUCTURE OR A BODY SURFACE FROM A REMOTE LOCATION

CROSS-REFERENCE TO RELATED APPLICATIONS

This is a continuation-in-part of U.S. patent application Ser. No. 13/865,901, filed Apr. 18, 2013, now U.S. Pat. No. 9,037,217; which is a continuation-in-part of U.S. patent application Ser. No. 13/573,100, filed Aug. 20, 2012, now U.S. Pat. No. 8,903,468; which is a continuation-in-part of U.S. patent application Ser. No. 12/925,518, filed Oct. 22, 2010, now U.S. Pat. No. 8,452,372; which claims the benefit of U.S. Provisional Application No. 61/455,111, filed Oct. 13, 2010; the disclosure of each of which is hereby incorporated by reference as if set forth in their entirety herein.

FIELD OF THE INVENTION

The present invention relates to methods and systems for laser coagulation of the eye or a body surface. More particularly, the present invention relates to non-invasive and non-contact methods and systems for laser coagulation of predetermined portions of the biological organism in the eye; particularly, the retina, or an external body surface

BACKGROUND OF THE INVENTION

As is well known in the art, various eye disorders, such as diabetic retinopathy, vascular occlusion, neovascularization and age macular degeneration, can, and in most instances will, have an adverse effect on the retina. Indeed, if not treated at the appropriate stage, noted diseases, particularly, diabetic retinopathy, can lead to severe losses in vision.

Various methods and systems have thus been developed to aid in the diagnosis of the noted eye diseases. The method often employed by an eye care specialist, such as an ophthalmologist, is to examine the ocular fundus (the inside back surface of the eye containing the retina, blood vessels, nerve fibers, and other structures) with an ophthalmoscope.

The ophthalmoscope is a small, hand-held device, which, when appropriately positioned, shines light through a subject's pupil to illuminate the fundus. By properly focusing the light reflected from the subject's fundus, an examiner can observe the fundus structures.

As is well known in the art, examination of the ocular fundus can also be achieved using a fundus or slit lamp camera. Illustrative are the apparatus and systems disclosed in U.S. Pat. Nos. 5,713,047, 5,943,116, 5,572,266, 4,838, 680, 6,546,198, 6,636,696, 4,247,176, 5,742,374 and 6,296, 358.

Various method and systems have also been developed to treat eye disorders, such as diabetic retinopathy, glaucoma and age macular degeneration. One known method of treating the noted eye disorders, as well as retinal detachment, is laser coagulation of predetermined biological structures of the eye, such as the retina.

As is well known in the art, during laser coagulation of an eye structure, laser energy is transmitted to the structure to effect coagulation thereof. A typical laser coagulation system thus includes a laser energy or beam source, such as a beam projector, a slit image projector or lamp for forming a slit image on the eye, and observation equipment for observing the slit image and laser spot(s) in the eye. Illustrative are the laser coagulation systems disclosed in U.S. Pat. Nos. 4,759,360 and 4,736,744.

A major drawback associated with each of the noted conventional systems, as well as most known laser coagulation systems (and associated methods), is that the conventional slit lamp systems require a contact lens to neutralize the refractive power of the cornea. A contact lens is also necessary to provide a variable field of view of the retina up to 130°.

As is well known in the art, the contact lens must be appropriately positioned on the surface of the cornea and held at the desired position by the specialist, e.g., surgeon, while looking through the slit lamp microscope.

During this conventional laser coagulation procedure, the contact lens is positioned on the cornea, and held in position by the surgeon so as to permit the surgeon to view the retina through the slit lamp microscope during the laser application to the retina. In all conventional contact systems, the field of view is limited (e.g., maximum 50-60 degrees) and the surgeon is required to move the contact lens from one side of the eye to the other side of the eye during the procedure, and the patient is also required to move his or her eye, in order to permit the surgeon to see the peripheral retina.

There are several drawbacks associated with the use of a contact lens during laser coagulation. A major drawback is that the use of a contact lens requires topical anesthesia and a dilated pupil for laser application. As is well known in the art, a contact lens can, and in many instances will, cause corneal abrasion on an anesthetized cornea.

A further drawback associated with conventional laser coagulation procedures is that the laser procedures are dependent on the steadiness of the physician's hands and the subject's head.

Another apparatus that is often used for laser energy delivery to the peripheral retina is the indirect ophthalmoscope. Use of the indirect ophthalmoscope requires a physician to hold an appropriate convex lens in front of the eye (pupil) with one hand to focus the laser beam on the retina, while the eye is indented with another hand to bring the peripheral retina into the field of view for laser application.

In the indirect ophthalmoscopy technique, which is an alternative conventional method, the physician (i.e., surgeon) does not place a contact lens on the cornea, but rather he or she has to indent the peripheral part of the eye with an indenter (or scleral depressor) to bring the peripheral retinal areas into view, and additionally, the patient has to move the eye side to side.

Although laser delivery with an indirect ophthalmoscope eliminates the need for a contact lens, there are still drawbacks and disadvantages associated with use of an indirect ophthalmoscope. A major drawback is that during laser delivery (and, hence, coagulation of a desired eye structure), the ophthalmoscope is often carried on the physician's head for 30-60 mins. This extended period causes extreme fatigue for the physician.

The indentation of the eye for the extended period is also very unpleasant for the subject or patient.

A further drawback associated with the use of an indirect ophthalmoscope for laser coagulation is that the indirect ophthalmoscope does not provide a retained record or documentation for future evaluation. Further, in most instances, the subject typically requires subsequent fundus photography.

None of the abovedescribed conventional methods are suitable for remote laser application because they are limited in their field of view (typically 50-60 degrees). Also, the eye movement that is needed with these systems to view the entire retina renders them unsuitable for remote applications.

It would thus be desirable to provide non-contact systems and methods for laser coagulation of eye structures to treat eye disorders, and are capable of being effectively utilized to treat patients located at a remote site.

It is therefore an object of the present invention to provide non-contact systems and methods for laser coagulation of eye structures that substantially reduce or overcome the noted drawbacks and disadvantages associated with conventional contact-based laser coagulation systems and methods.

It is another object of the present invention to provide non-contact apparatus, systems and methods for laser imaging and coagulation of an eye structure.

It is another object of the present invention to provide non-contact apparatus, systems and methods for laser imaging and coagulation of the retina and its periphery to treat retina and choroideal disorders and/or diseases.

SUMMARY OF THE INVENTION

The present invention is directed to laser imaging and coagulation apparatus, systems and methods that allow an eye specialist, e.g., an ophthalmologist or surgeon, to perform laser surgery on an eye structure, e.g. retina, with an integral laser imaging and coagulation apparatus disposed at a first (i.e. local) location from a control system disposed at a second (i.e. remote) location, e.g., a physician's office. The laser imaging and coagulation apparatus, systems and methods of the invention thus make it possible for an ophthalmologist to screen and perform laser surgery to treat various eye disorders, including, without limitation, diabetic retinopathy, vascular occlusion, neovascularization and age macular degeneration from a geographically remote location.

In one embodiment of the invention, the laser coagulation system includes (i) at least a first laser-imaging system disposed at a first location, the first laser-imaging system including a first laser-imaging apparatus, a photoacoustic system, a first processor and a local control module, the first laser-imaging apparatus including a wide angle digital image acquisition system for acquiring digital images of a subject's eye structure and a laser generation system for transmitting an aiming laser beam and at least a first coagulation laser beam to the eye structure, the first coagulation laser beam having a first laser energy, the photoacoustic system being configured to measure temperature of eye structure tissue subjected to the first laser energy, the local control module including local operation, local operation and performance simulation and local safety and verification sub-modules; and (ii) a central control system disposed at a remote site, the central control system including a second processor and a remote control module, the remote control module including remote operation, remote operation and performance simulation, and remote safety and verification sub-modules, the remote operations sub-module being configured to facilitate communications between a remote physician and the remote processor, and perform a laser coagulation procedure on the eye structure in an actual control mode.

In some embodiments of the invention, the local operation sub-module is configured to acquire at least a first eye structure image from the digital image acquisition system and transmit the first eye structure image to the remote site, receive a target laser transmission area and laser transmission parameters from a remote physician, apply an active contour algorithm to partition the first eye structure image into a grid map, perform a scatter laser (focal or grid) coagulation of the eye structure under the remote physician's command, acquire a plurality of post-procedure eye structure images, and transmit the post-procedure eye structure images to the remote site for evaluation and verification of treatment.

In some embodiments, the remote operations sub-module is further configured to execute a virtual treatment of the eye structure and perform a test surgical procedure in association with the local operation and performance simulation sub-module.

In some embodiments, the remote operation and performance simulation sub-module is configured to test performance parameters of the local operation module and perform virtual treatment of the eye structure by the remote physician.

In some embodiments of the invention, the photoacoustic system is configured to control the laser generation system.

In one embodiment of the invention, the eye structure comprises the retina.

In some embodiments of the invention, the laser coagulation system also includes eye tracking means for tracking movement of the eye.

In some embodiments of the invention, the laser coagulation system also includes facial recognition means for identifying and/or verifying the identity of the subject.

In one embodiment, communication by and between the central control system and the laser-imaging apparatus is achieved via the Internet®.

In another embodiment, the laser coagulation system includes:

a local control system disposed at a first location and a central control system disposed at a remote site, the remote site being at a second location;

at least a first laser-imaging system disposed at the first location, the laser-imaging system including a laser-imaging apparatus, a first processor and a local control module;

the laser-imaging apparatus including a digital image acquisition system configured to acquire digital images of the eye structure or the body surface, the local control module including local operation, local operation and performance simulation, and local safety and verification sub-modules;

a laser generation system configured to generate and transmit at least a first aiming laser beam and at least a first coagulation laser beam, and means for controlling the digital image acquisition system and the laser generation system;

a central control system disposed at the remote site, the central control system including a second processor and a remote control module, the remote control module including remote operation, remote operation and performance simulation, and remote safety and verification sub-modules; and the remote operation sub-module being configured to facilitate communications between a remote physician and the second processor, and perform a laser coagulation procedure on the eye structure or the body surface in an actual control mode, the remote operation sub-module including a touchscreen interface configured to enable the remote physician to draw a target laser treatment area or areas on a digitized image of the eye structure or the body surface.

In yet another embodiment, the laser coagulation system includes:

a local control system disposed at a first location and a central control system disposed at a remote site, the remote site being at a second location, the local control system being operatively coupled to the central control system by means of a computer network;

at least a first laser-imaging system disposed at the first location, the laser-imaging system including a laser-imaging apparatus, a laser generation system, a first computing device with a first processor, and a local control module;

the laser-imaging apparatus including a digital image acquisition system configured to acquire a digitized image of the eye structure or the body surface, the local control module including local operation, local operation and performance simulation, and local safety and verification sub-modules, the local operation sub-module configured to acquire the digitized image of the eye structure or the body surface from the digital image acquisition system and transmit the digitized image to the remote site;

the laser generation system including an aiming laser configured to generate and transmit an aiming laser beam to the eye structure or the body surface, and a treatment laser configured to generate and transmit at least a first coagulation laser beam to the eye structure or the body surface;

the central control system including a second computing device with a second processor, and a remote control module, the remote control module including remote operation, remote operation and performance simulation, and remote safety and verification sub-modules; and the remote operation sub-module being configured to facilitate communications between a remote physician and the second processor of the second computing device, and perform a laser coagulation procedure on the eye structure or the body surface in an actual control mode in which the treatment laser is configured to transmit the first coagulation laser beam to the eye structure or the body surface.

In some embodiments of the invention, the first laser-imaging system further includes an image recognition sensor configured to capture images of a patient at the first location so that an identity of the patient or an identity of a body portion of the patient is capable of being identified and verified prior to the laser coagulation procedure being performed on the eye structure or the body surface in the actual control mode.

In some embodiments, the image recognition sensor is operatively coupled to the first computing device, the first computing device being specially programmed to compare a first reference digital image of the patient captured by the image recognition sensor at a first time to a second digital image of the patient captured by the image recognition sensor at a second subsequent time, and to determine if the second digital image of the patient matches or substantially matches the first reference digital image of the patient (i.e., the second digital image of the patient substantially matches the first reference digital image of the patient when there are only minor differences between the two images, e.g., a blemish on the face of patient that appears in the second digital image, but not in the first reference digital image).

In some embodiments, when the first computing device determines that the second digital image of the patient substantially matches the first reference digital image of the patient, the first computing device is specially programmed to generate a matched image confirmation notification that is sent to the second computing device at the remote site in order to inform the remote physician that the patient has been identified and verified; and, when the first computing device determines that the second digital image of the patient does not substantially match the first reference digital image of the patient, the first computing device is specially programmed to generate a non-matching image notification that is sent to the second computing device at the remote site in order to inform the remote physician that the patient has not been properly identified and verified.

In some embodiments, when the first computing device determines that the second digital image of the patient does not substantially match the first reference digital image of the patient, the first computing device is further specially programmed to automatically lock out the treatment laser so that the treatment laser is not capable of being fired.

In some embodiments, the image recognition sensor is in the form of a multispectral camera configured to capture the images of the patient using both visible light and infrared light.

In some embodiments, the first laser-imaging system further includes a voice recognition sensor configured to capture speech waveforms generated by the patient at the first location so that an identity of the patient is capable of being identified and verified prior to the laser coagulation procedure being performed on the eye structure or the body surface in the actual control mode.

In some embodiments, the voice recognition sensor is operatively coupled to the first computing device, the first computing device being specially programmed to compare a first reference speech waveform of the patient captured by the voice recognition sensor at a first time to a second speech waveform of the patient captured by the voice recognition sensor at a second subsequent time, and to determine if the second speech waveform of the patient matches or substantially matches the first reference speech waveform of the patient (i.e., the second speech waveform of the patient substantially matches the first reference speech waveform of the patient when there are only minor differences between the two speech waveforms, e.g., a minor difference in the tone of the speech).

In some embodiments, when the first computing device determines that the second speech waveform of the patient matches or substantially matches the first reference speech waveform of the patient, the first computing device is specially programmed to generate a matched speech confirmation notification that is sent to the second computing device at the remote site in order to inform the remote physician that the patient has been identified and verified; and, when the first computing device determines that the second speech waveform of the patient does not match or substantially match the first reference speech waveform of the patient, the first computing device is specially programmed to generate a non-matching speech notification that is sent to the second computing device at the remote site in order to inform the remote physician that the patient has not been properly identified and verified.

In some embodiments, when the first computing device determines that the second speech waveform of the patient does not substantially match the first reference speech waveform of the patient, the first computing device is further specially programmed to automatically lock out the treatment laser so that the treatment laser is not capable of being fired.

In some embodiments, the voice recognition sensor is in the form of a microphone configured to capture the speech waveforms generated by the patient over a speech frequency range between 50 Hertz and 5,000 Hertz.

In still another embodiment, the laser coagulation system includes:

a local control system disposed at a first location and a central control system disposed at a remote site, the remote site being at a second location, the local control system being operatively coupled to the central control system by means of a computer network;

at least a first laser-imaging system disposed at the first location, the laser-imaging system including a laser-imaging apparatus, a laser generation system, a first computing device with a first processor, and a local control module;

the laser-imaging apparatus including a digital image acquisition and storage system configured to take and store digital images of the eye structure or the body surface, the digital image acquisition and storage system further including means for transmitting digital images;

the laser generation system including an aiming laser configured to generate and transmit an aiming laser beam to the eye structure or the body surface, and a treatment laser configured to generate and transmit at least a first coagulation laser beam to the eye structure or the body surface, and means for controlling the digital image acquisition and storage system and the laser generation system;

the local control module including a local operation sub-module, a local operation and performance simulation sub-module, the local operation sub-module configured to acquire at least a first digitized image of the eye structure or the body surface from the digital image acquisition and storage system and transmit the first digitized image to the remote site, the local operation sub-module further configured to receive a target laser transmission area or areas and laser transmission parameters from a remote physician, and determine a treatment area or pattern of spots on the first digitized image for application of the first coagulation laser beam, the local operation sub-module additionally configured to perform a laser coagulation of the eye structure or the body surface under the remote physician's command in which the first coagulation laser beam is applied to the treatment area or each of the spots in the pattern, the local operation and performance simulation sub-module configured to facilitate the testing of the system prior to its operation in an actual control mode by replacing an actual eye structure or body surface of the subject with the first digitized image of the subject's eye structure or body surface;

the central control system being in communication with the laser-imaging apparatus, the central control system including a remote control module and a second computing device with a second processor configured to receive and process command signals from the remote physician and transmit the command signals to the local control module; and the remote control module including a remote operation sub-module configured to facilitate communications between the remote physician and the second processor of the second computing device, the remote operation sub-module, in association with the local operation and performance simulation sub-module, further configured to execute a virtual treatment of the eye structure or the body surface, perform a test surgical procedure, and perform a fully automated and continuous laser coagulation procedure over the entire area of the eye structure or the body surface in the actual control mode in which the treatment laser is configured to transmit the first coagulation laser beam to the eye structure or the body surface In yet another embodiment, the laser coagulation system includes:

a local control system disposed at a first location and a central control system disposed at a remote site, the remote site being at a second location;

at least a first laser-imaging system, the laser-imaging system including a laser-imaging apparatus, a first processor and a local control module;

the laser-imaging apparatus including a wide angle digital image acquisition and storage system configured to take and store digital images of the retina, the digital image acquisition and storage system including at least one retinal viewing camera that provides a field of view of the retina in a range between 160° and 200°, the digital image acquisition and storage system further including means for transmitting digital images;

a laser generation system configured to generate and transmit at least a first aiming laser beam and at least a first coagulation laser beam, and means for controlling the digital image acquisition and storage system and the laser generation system;

the local control module including a local operation sub-module, a local operation and performance simulation sub-module, and a local safety and verification sub-module, the local operation sub-module configured to acquire at least a first retinal image of the retina from the digital image acquisition and storage system and transmit the first retinal image to the remote site, the local operation sub-module further configured to receive a target laser transmission area and laser transmission parameters from a remote physician, and determine a pattern of spots on the first retinal image for application of the first coagulation laser beam, the local operation sub-module additionally configured to perform a scatter laser coagulation of the retina under the remote physician's command in which the first coagulation laser beam is applied to each of the spots in the pattern, acquire a plurality of post-procedure retinal images, and transmit the post-procedure retinal images to the remote site for evaluation and verification of treatment, the local operation and performance simulation sub-module configured to facilitate the testing of the system prior to its operation in an actual control mode by replacing an actual eye of the subject with a digitized fundus image of the subject's eye;

the central control system being in communication with the laser-imaging apparatus, and including a remote control module and a second processor configured to receive and process command signals from the remote physician and transmit the command signals to the local control module;

the remote control module including a remote operation sub-module configured to facilitate communications between the remote physician and the second processor, execute a virtual treatment of the retina, perform a test surgical procedure, and perform a fully automated and continuous laser coagulation procedure over the entire area of the retina in the actual control mode;

the remote control module further including a remote operation and performance simulation sub-module and a remote safety and verification sub-module, the remote operation and performance simulation sub-module configured to test performance parameters of the local operation module and perform a treatment simulation of the retina by the remote physician while simulating eye movement of the subject by displacing the digitized fundus image of the subject's eye in accordance with a plurality of random variables;

the local and remote safety and verification sub-modules including physical, logical and medical safety constraints for safe operation of the system; and wherein the system for laser coagulation of the retina is in the form of a non-contact system that does not require the use of a contact lens.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
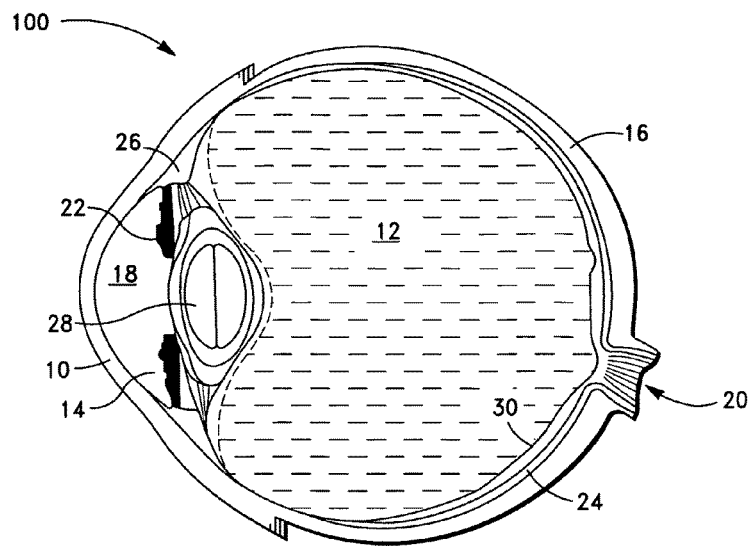
FIG. 1 is an illustration of a human eye showing the major structures thereof.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "a laser image" includes two or more such images and the like.

DEFINITIONS

The terms "eye disorder" and "eye disease" are used interchangeably herein and mean and include, without limitation, diabetic retinopathy, vascular occlusion, neovascularization, retinal detachment, neoplastic tissue, ischemic retina, retinopathy of prematurity and age related macular degeneration.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As will readily be appreciated by one having ordinary skill in the art, the present invention substantially reduces or eliminates the disadvantages and drawbacks associated with conventional systems and methods for coagulating eye structures to treat eye disorders.

In overview, the present disclosure is directed to laser imaging and coagulation apparatus, systems and methods that allow an eye specialist, e.g., an ophthalmologist or surgeon, to perform laser retinal surgical procedures, such as laser or tissue coagulation, with an integral laser imaging and coagulation apparatus disposed at a first (i.e. local) location from a control system disposed at a second (i.e. remote) location, e.g., a physician's office.

By the term "laser coagulation", as used herein, it is meant to mean and include, without limitation, selective absorbance of transmitted light energy (having a visible green wavelength) by hemoglobin in biological tissue and, hence, sealing of blood vessels in the tissue. In a preferred embodiment of the invention, the wavelength of the transmitted energy (referred to herein as a "treatment or coagulative laser beam") is in the range of approximately 400-1650 nm, more preferably, in the range of approximately 530-670 nm.

Although the present invention is directed to thermotherapy of biological tissue by laser energy, it is to be understood the invention is not limited to such form of energy. Indeed, as will readily be appreciated by one having ordinary skill in the art, the thermotherapy of biological tissue described herein, i.e. coagulation of selective eye structures, can also be achieved via the application of electromagnetic radiation, and radio frequency and ultrasound energy.

It is further to be understood that, although the biological tissue subject to the thermotherapy (i.e. coagulation), in accordance with the present invention, comprises the retina, the invention is not limited solely to thermotherapy of the retina. According to the invention, the thermotherapy of the present invention can be employed to coagulate any eye structure.

The laser-imaging apparatus, systems and methods of the invention, and laser energy transmitted thereby, can thus be employed to treat various eye disorders, including, without limitation, diabetic retinopathy, vascular occlusion, neovascularization, retinal detachment, neoplastic tissue, ischemic retina, retinopathy of prematurity and age related macular degeneration.

The laser-imaging apparatus, systems and methods of the invention, and laser energy transmitted thereby, can also be readily employed in refractive surgical procedures to, for example, perform corneal surface ablation using an eximer or femtosecond laser, LASIK procedures, and/or lid surface and surrounding tissue tightening using an infrared laser.

The laser-imaging apparatus, systems and methods of the invention, and laser energy transmitted thereby, can also be readily employed in cosmetic surgical procedures to, for example, remove skin lesions and perform skin resurfacing.

Before describing the invention in detail, the following brief description of the various anatomical features of the eye is provided, which will help in the understanding of the various features of the invention:

Referring to FIG. 1, the cornea 10, which is the transparent window that covers the front of the eye 100, is a lens-like structure that provides two-thirds of the focusing power of the eye.

The cornea 10 is slightly oval, having an average diameter of about 12 mm horizontally and 11 mm vertically. The central thickness of the cornea 10 is approximately 550 µm.

The sclera 16 is the white region of the eye, i.e. posterior five sixths of the globe. It is the tough, avascular, outer fibrous layer of the eye that forms a protective envelope. The sclera is mostly composed of dense collagen fibrils that are irregular in size and arrangement (as opposed to the cornea). The extraocular muscles insert into the sclera behind the limbus.

The sclera 16 can be subdivided into 3 layers: the episclera, sclera proper and lamina fusca. The episclera is the most external layer. It is a loose connective tissue adjacent to the periorbital fat and is well vascularized.

The sclera proper, also called tenon's capsule, is the layer that gives the eye 100 its toughness. The sclera proper is avascular and composed of dense type I and III collagen.

The lamina fusca is the inner aspect of the sclera 16. It is located adjacent to the choroid and contains thin collagen fibers and pigment cells.

The pars plana is a discrete area of the sclera 16. This area is a virtually concentric ring that is located between 2 mm and 4 mm away from the cornea 10.

The vitreous humor or vitreous 12 is the largest chamber of the eye 100 (i.e. ~4.5 ml). The vitreous 12 is a viscous transparent gel composed mostly of water. Unlike the fluid contained in the frontal parts of the eye (e.g., aqueous humor, discussed below), which are continuously replenished, the transparent gel in the vitreous chamber is stagnant.

As is well known in the art, the vitreous humor 12 also contains a random network of thin collagen fibers, mucopolysaccharides and hyaluronic acid.

The aqueous humor 14 occupies the anterior chamber 18 of the eye 100. The aqueous humor 14 has a volume of about 0.6 mL and provides nutrients to the cornea 10 and lens 28.

One of the most important functions of the aqueous humor 14 is to maintain TOP by the rate of its production and drainage.

The additional parts of the eye that are illustrated in FIG. 1 comprise the uvea, and structures thereof, lens 28 and retina 30.

The uvea refers to the pigmented layer of the eye 100 and is made up of three distinct structures: the iris 22, ciliary body, and choroid 24. The iris 22 is the annular skirt of tissue in the anterior chamber 18 that functions as an aperture. The pupil is the central opening in the iris 22.

The ciliary body is the 6 mm portion of uvea between the iris 22 and choroid 24. The ciliary body is attached to the sclera 16 at the scleral spur. It is composed of two zones: the anterior 2 mm pars plicata, which contains the ciliary muscle 26, vessels, and processes, and the posterior 4 mm pars plana.

The ciliary muscle 26 controls accommodation (focusing) of the lens 28, while the ciliary processes suspend the lens 28 (from small fibers, i.e. zonules) and produce the aqueous humor 14 (the fluid that fills the anterior and posterior chambers and maintains intraocular pressure).

The choroid 24 is the tissue disposed between the sclera 16 and retina 30. The choroid 24 is attached to the sclera 16 at the optic nerve 20 and scleral spur. This highly vascular tissue supplies nutrients to the retinal pigment epithelium (RPE) and outer retinal layers.

The layers of the choroid 24 (from inner to outer) include the Bruch's membrane, choriocapillaris and stroma. Bruch's membrane separates the RPE from the choroid 24 and is a permeable layer composed of the basement membrane of each, with collagen and elastic tissues in the middle.

The crystalline lens 28, located between the posterior chamber and the vitreous cavity, separates the anterior and posterior segments of the eye 100. Zonular fibers suspend the lens from the ciliary body and enable the ciliary muscle to focus the lens 28 by changing its shape.

The retina 30 is the delicate transparent light sensing inner layer of the eye 100. The retina 30 faces the vitreous and consists of two basic layers: the neural retina and retinal pigment epithelium. The neural retina is the inner layer. The retinal pigment epithelium is the outer layer that rests on Bruch's membrane and choroid 24.

As indicated above, conventional slit lamp systems, which are often employed to treat various eye disorders, such as diabetic retinopathy, require a contact lens to neutralize the refractive power of the cornea and to provide a variable field of view of the retina.

The length of time to perform a surgical procedure with a conventional slit lamp system is also presently in the range of 30 minutes to an hour. There is thus an increased percentage of probable error due to the laser photo-coagulation being controlled manually, i.e. by the physician's hand, and the potential eye movements from the patient during this extended period of time.

The present invention substantially reduces or eliminates the disadvantages and drawbacks associated with conventional slit lamp systems and associated methods. As discussed in detail herein, the laser-imaging apparatus include means for taking and storing digital images of the target eye structure(s), which can be retrieved on a monitor for diagnosis and defining the area of treatment. In some embodiments, the laser-imaging apparatus (and systems) of the invention thus include a retinal camera (e.g., Topcon, Zeiss, Kowa or preferably a wide angle viewing system having an elliptical mirror), which, in some embodiments, is modified with a wide-angle lens.

A wide field scanning laser-imaging apparatus, such as the laser opthalmoscope disclosed in U.S. Pat. No. 5,815,242, can also be employed to provide images of the fundus, particularly, the retina. The noted laser-imaging apparatus can also be readily modified for laser coagulation procedures in one or multiple health care applications or additional vision care offices.

According to the invention, the viewing light can comprise a white light from a flush light, laser source or one or more scanning lasers with compensatory wavelengths in the range of approximately 190 nm-10,000 nm, more preferably, in the range of approximately 400-1060 nm, to obtain a fundus photograph.

According to the invention, the retinal camera is connected to laser transmission means (or a laser system) that is adapted to generate and transmit laser energy that is sufficient to coagulate any desired portion of the retina using a monitor's touch screen.

In a preferred embodiment of the invention, the laser-imaging apparatus incorporates aiming and treatment laser generating and transmission means into an existing camera (e.g., Topcon, Zeiss, etc.) or a wide angle viewing system/camera, such as the laser opthalmoscope disclosed in U.S. Pat. No. 5,815,242. The laser-imaging apparatus also includes control means for controlling the aiming and treatment laser means, and the camera.

Preferably, the transmitted laser beam passes through the optical path of the viewing apparatus (or system) and is preferably reflected off of an elliptical mirror in the camera (in which the imaging light is focused toward the pupil or slightly behind the pupil), providing a field of view greater than approximately 200°.

Figure 2:
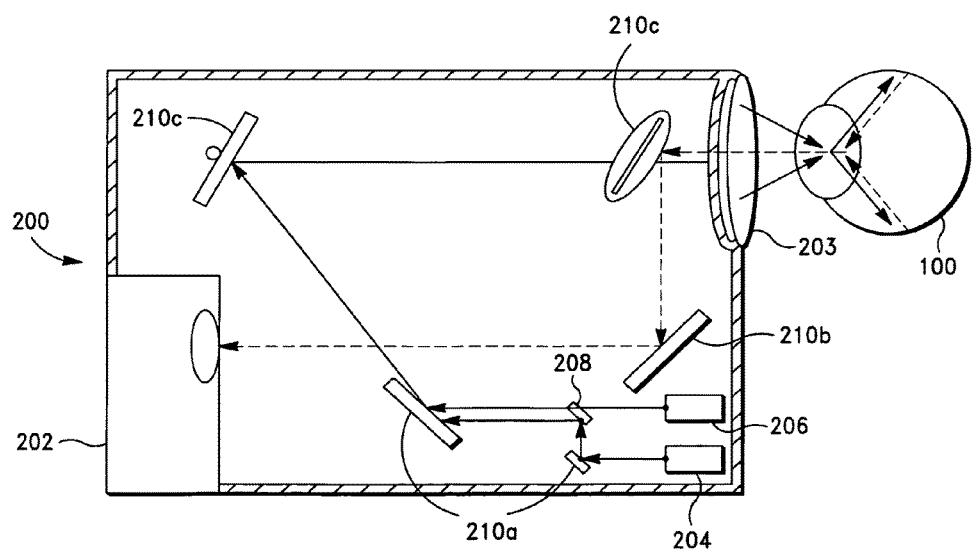
FIG. 2 is a schematic illustration of one embodiment of a laser-imaging apparatus, in accordance with the invention.

Referring now to FIG. 2, there is shown one embodiment of a laser-imaging apparatus of the invention. As illustrated in FIG. 2, the laser-imaging apparatus 200 includes a Topcon digital camera 202, scanning laser visualization means 204 and internal laser generation and transmission means (i.e. coagulation means) 206. The laser-imaging apparatus 200 further includes a refracting lens 203, at least one two-way mirror 208 and a plurality of appropriately positioned reflecting mirrors 201a-201c.

Figure 3:
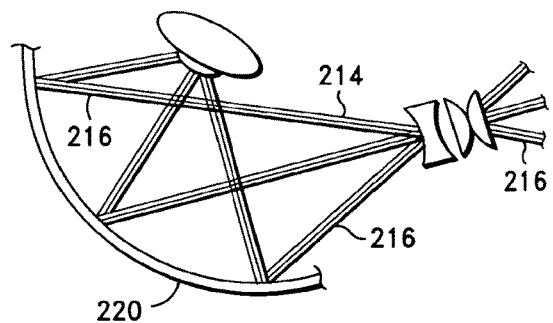
FIG. 3 is a schematic illustration of another embodiment of a laser-imaging apparatus, showing the elliptical mirror thereof, in accordance with the invention.

Referring now to FIG. 3, in an alternative embodiment, a wide angle camera equipped with an elliptical mirror 220 is employed. According to the invention, the illustrated wide angle camera provides an improved range of between approximately 150° and approximately 200°, inclusive, (or an improved range between 150° and 200°, inclusive) of the retina for optimal treatment.

In some embodiments, the concave, elliptical mirror 220 illustrated in FIG. 3 is configured to oscillate (or wobble) slightly in order to shift the focal point of the mirror 220 slightly from one side of the pupil to the other side, thereby permitting the scanning light (e.g., low coherent wavelengths, etc.) inside the eye to cover a larger peripheral field than possible without oscillation. An exemplary imaging system for imaging the central and peripheral retina, which employs such an oscillating concave mirror, is disclosed in Applicant's U.S. Pat. No. 8,070,289; which is incorporated by reference herein in its entirety.

In other embodiments, the concave, elliptical mirror 220 illustrated in FIG. 3 is stationary and is not configured to oscillate or wobble. It is also to be understood that the concave mirror 220 can be provided in the form of circular mirror, as well as an elliptical mirror.

FIG. 3 shows the path of the viewing/imaging scanning laser beams 214 as they are reflected and pass through the focal point of the mirror behind the pupil (Black) toward the retina. As illustrated in FIG. 3, the coagulative laser beam 216 preferably passes through the same path as the viewing/imaging beams 214.

In some embodiments of the invention, the laser-imaging apparatus of the invention also includes an optical coherence tomography (OCT) means.

Preferably, the rays reflected back from the retina pass through the same pathway and form a digital image that can be observed on the monitor.

According to the invention, the coagulative laser beam is also scanned over the retinal area via the same light path as used for the observation and documentation.

The integration of the aiming and treatment laser generating and transmission means with a camera requires the introduction of precision motorized optical fixtures. An opto-mechanical system having an integral control system is thus provided to control and/or position the target spot of the laser beam(s) in x and y directions within the eye. The system is designed and adapted to interface with joystick commands and/or computer/monitor touch screen commands, for local and remote control of the aiming and treatment (or coagulative) laser transmissions, respectively.

In some embodiments of the invention, the control means for positioning the laser transmissions (or beams) within the eye consists of two main components. The first component is adapted to move the beams in the x-direction. The second component is adapted to move the beams in the y-direction.

Preferably, movement in the y-direction is provided by a mirrored surface disposed in the optical path of the camera. This y-direction, motorized fixture provides precise movement of the mirrored surface, while still allowing diagnostic and treatment images to be seen through the retinal camera.

In some embodiments of the invention, producing the x-direction movement involves physically moving the laser unit; the movement of the laser being either translational or rotational. Various conventional means of motorized movement can also be employed to provide movement in the x-direction.

In a preferred embodiment, the laser-imaging apparatus is in communication with another remote system via the Internet®, whereby the laser-imaging apparatus can be controlled by a physician at the remote site (e.g., medical center).

According to the invention, location of laser energy or beam application can be from 5-200° of the retina. In some embodiments, location of laser energy application is preferably 30-200° of the retina.

In some embodiments of the invention, the transmitted coagulative laser energy (or beam(s)) has a wavelength in the range of approximately 400-1650 nm, more preferably, in the range of approximately 530-670 nm. The laser (or laser energy) can also be transmitted in a pulsed manner or continuously.

According to the invention, the laser spot size can be in the range of approximately 10 micron-1500 micron.

According to the invention, exposure time of the laser energy application can be in the range of approximately 1 femto-seconds to 1000 seconds.

In some embodiments of the invention, the laser-imaging apparatus 200 includes a photoacoustic system that can measure the temperature inside the eye tissue during and after laser scanning. A preferred photoacoustic system is disclosed in Applicant's U.S. Pat. No. 8,121,663; which is incorporated by reference herein in its entirety.

As set forth in detail in the '663 patent, the photoacoustic system is adapted to record the sonic waves that are generated by heating eye tissue, e.g. retina tissue. This provides precise information of the temperature generated as a result of the laser transmission, i.e. coagulative laser energy.

Advantageously, the photoacoustic system enables the temperature generated at the treatment site to be measured.

As a result, the system is capable of balancing the energy of the laser system so that the coagulation is performed in a uniform fashion at the desired area, without such balancing one could have some lesions stronger than others depending on the degree of the pigmentation of the retina at the particular site (i.e., if the site absorbs more laser light).

Figure 4:
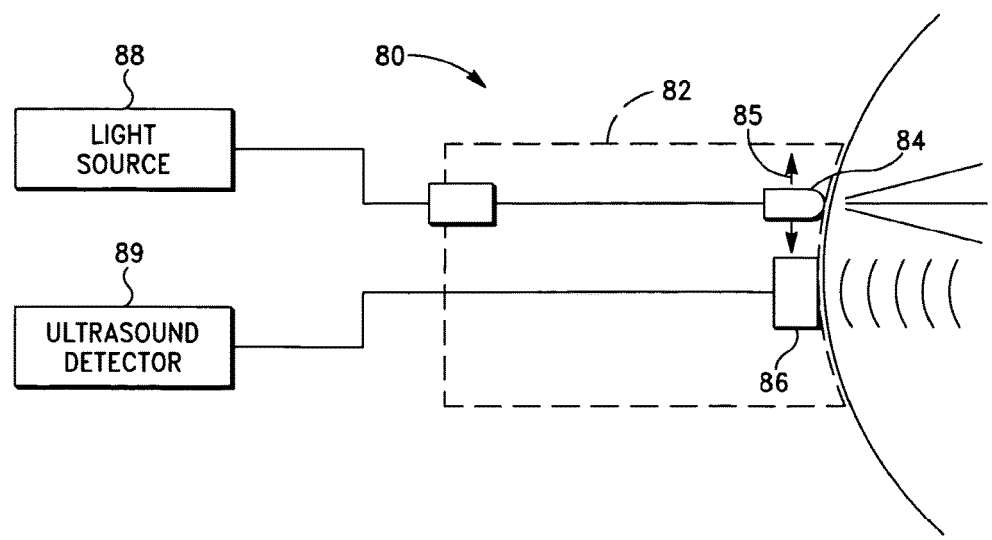
FIG. 4 is a schematic illustration of a photoacoustic system, in accordance with the invention.

Referring now to FIG. 4, there is shown one embodiment of a photoacoustic system 80. As illustrated in FIG. 4, the photoacoustic system 80 includes a laser source 88, an ultrasonic detector 89, and a probe module 82. The probe module 82 includes an objective lens structure 84, which is preferably coupled to the light source 88 via a fiber optic connection or other light transmitter. Alternatively, the light source can be incorporated into the probe module 82.

According to the invention, the light source 88 can comprise a laser, laser diode or superluminescent diode (SLD), as appropriate for generating the desired light wavelength and intensity. The light can also be delivered as pulses or as modulated radiation.

As further illustrated in FIG. 4, the probe module 82 further contains an ultrasound transducer 86 that is adapted to detect the photoacoustic waves that are generated as a result of the absorption of energy from the light emitted by the objective lens structure 84. The ultrasound transducer 86 is in contact with the eye 100 or an eyelid drawn over the eye.

As light is delivered as pulses or as modulated radiation, pulses or modulating acoustic signals are generated and returned to the ultrasound transducer 86 in probe module 82.

According to the invention, localization of the source of photoacoustic signals can be achieved in various manners. First, localization can be accomplished by directing the beam from objective lens structure 84 in specific directions, by moving that structure with micromechanical actuators, as shown diagrammatically at 85 in FIG. 4, thus targeting a particular line of points in the eye.

Furthermore, by suitable optics included in objective lens structure 84, the focal point of the emitted light may be moved within the eye to a desired point, such as a point along the retina vasculature, to selectively generate acoustic signals at that desired point. Because the eye is optically transmissive relative to soft tissue, beam focusing and beam directing are likely to be more accurately performed in the eye, than is the case is soft tissue elsewhere in the body.

To further assist in directionally capturing the photoacoustic signals generated within the eye, a directional transducer array can be used as transducer 86, to control the directionality of reception of ultrasonic energy, thus further localizing upon a desired source of thermoacoustic signals. Thus, by targeting the focal point of the illuminating light, and also directionally targeting the reception of ultrasonic signals by the transducer array, thermoacoustic signals from a particular location, such as along the retina, may be specifically targeted.

Overview of Laser-Imaging System

Figure 5:
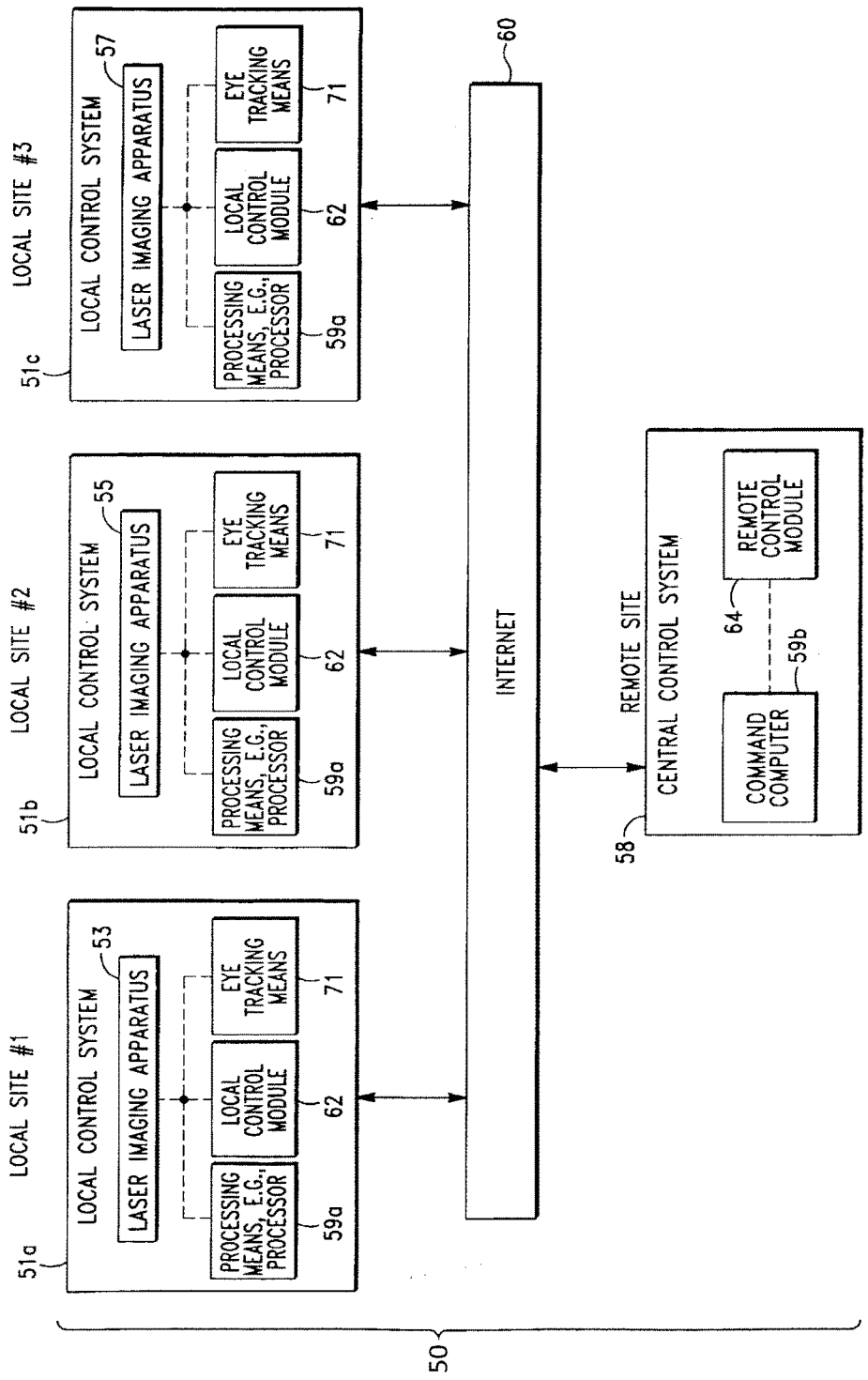
FIG. 5 is a schematic illustration of one embodiment of a laser-imaging system, in accordance with the invention.

Referring now to FIG. 5, there is shown a schematic diagram of a laser-imaging system 50, according to one embodiment of the invention. As illustrated in FIG. 5, the system 50 includes at least one, preferably, multiple local systems 52, 54, 56 disposed at local sites 51*a*, 51*b*, 51*c*; each system 52, 54, 56 including a laser-imaging apparatus (denoted "53", "55" and "57"), such as the apparatus 200 shown in FIG. 2. In a preferred embodiment of the invention, each laser-imaging apparatus 53, 55, 57 includes a photoacoustic system, such as system 80 discussed above.

Preferably, each laser-imaging apparatus 53, 55, 57 is preferably in communication with a local control module 62 and control-processing means 59*a*, such as a personal computer. Each of the modules described herein in conjunction with the embodiments of the laser-imaging systems 50, 50' may comprise one or more hardware components together with the requisite software to carry out the functionality performed thereby.

In some embodiments of the invention, at least the control-processing means 59*a* disposed at each local site 51*a*, 51*b*, 51*c* includes facial recognition means for identifying and/or verifying the identity of a subject or patient. Alternatively, in some embodiments, the control-processing means 59*b* disposed at the remote site 51*d* (discussed below) includes facial recognition means. In some embodiments both control-processing means 59*a*, 59*b* include facial recognition means.

In some embodiments of the invention, each local system 52, 54, 56 also includes eye tracking means 71 for measuring eye position(s) and movement. According to the invention, the eye tracking means 71 can be an integral component or feature of the laser-imaging apparatus 53, 55, 57 or a separate system or device.

Also disposed at each local site 51*a*, 51*b*, 51*c* during a laser procedure is a test subject or patient and a physician or technician.

As also illustrated in FIG. 5, the system 50 also includes a remote site 58 having a command computer 59*b* that is operatively connected to a remote control module 64. Also disposed at the remote site 58 during a laser procedure is a system operator (e.g., retinal surgeon).

As discussed in detail below, communication by and between the local sites 52, 54, 56 and the remote site 58 is preferably facilitated by the local and remote control modules 62, 64 and the Internet® 60.

In accordance with one embodiment of the invention, the sequence of interactions between the local sites 52, 54, 56 and remote site 58 comprises the following:

Fundus photograph is digitally transmitted to remote site;
Image is acquired by remote site and filed in the computer at remote site;
Eye is repositioned in front of the camera, fundus image is taken for pattern recognition and tracking, and transmitted to remote site, verified as matching previous, pre-existing image on file;
New image is selected and employed as simulator;
Spot size, power level, and time interval between each laser is chosen;
Tracking system (fail-safe) is checked;
Fundus laser treatment is performed in virtual mode to establish the desired laser coagulation; and
After choosing spot size and duration of laser application, power is adjusted to the lowest increment of energy that may or may not be able to create a response on the patient's eye. The power of the laser is incrementally increased until the test spot demonstrates the desired effect.

In a preferred embodiment, the optimum power and, hence, temperature required for a procedure is provided via the photoacoustic system. The photoacoustic system is further adapted to maintain the transmitted laser energy at a fixed, pre-selected level. This particularly results in a uniform coagulation of the retina.

Local and Remote Control Modules

Figure 6:
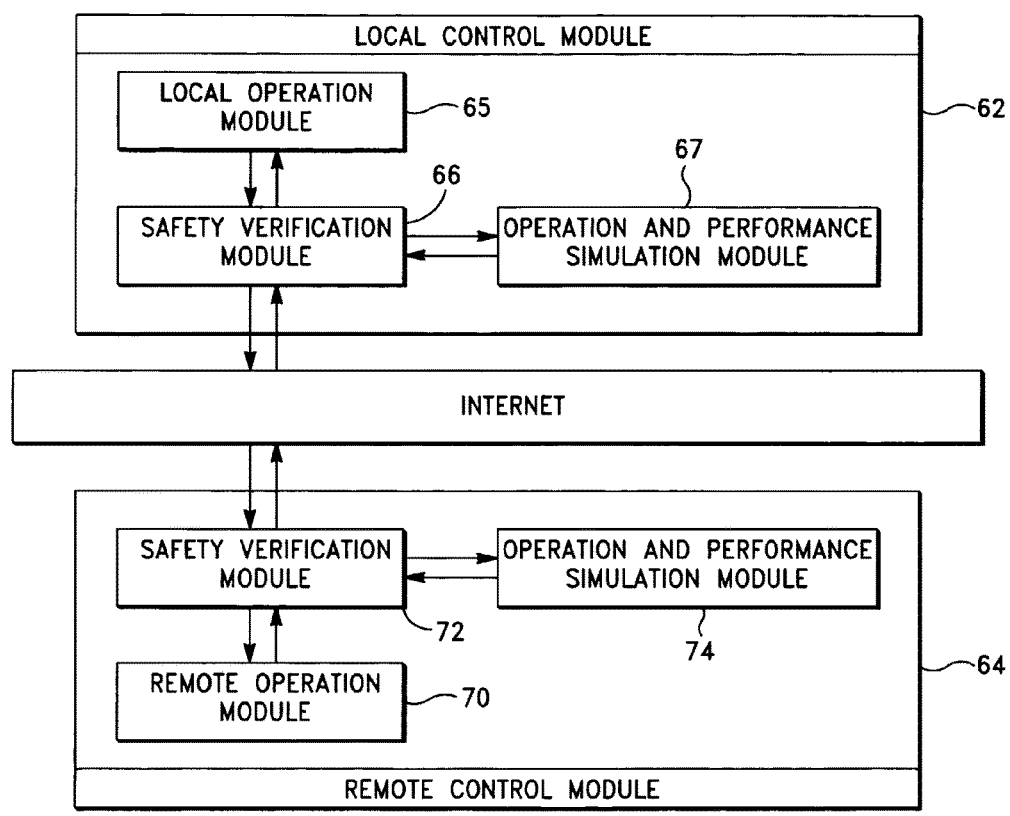
FIG. 6 is another schematic illustration of the laser-imaging system shown in FIG. 5, showing the local and remote modules thereof, in accordance with one embodiment of the invention.

Referring now to FIG. 6, there is shown a schematic diagram of a local control module 62 and a remote control module 64, according to one embodiment of the invention. As illustrated in FIG. 6, the local control module 62 preferably includes three sub-modules: an operation module 65, safety and verification module 66, and an operation and performance simulation module 67.

The remote control module 64 similarly includes three sub-modules: an operation module 70, safety and verification module 72, and an operation and performance simulation module 74.

Each of these sub-modules 65, 66, 67 is described below.

Local Operation Module

According to the invention, the local operation module 65 provides a local technician with an interface to a personal computer for data acquisition and eye treatment.

Figure 10:
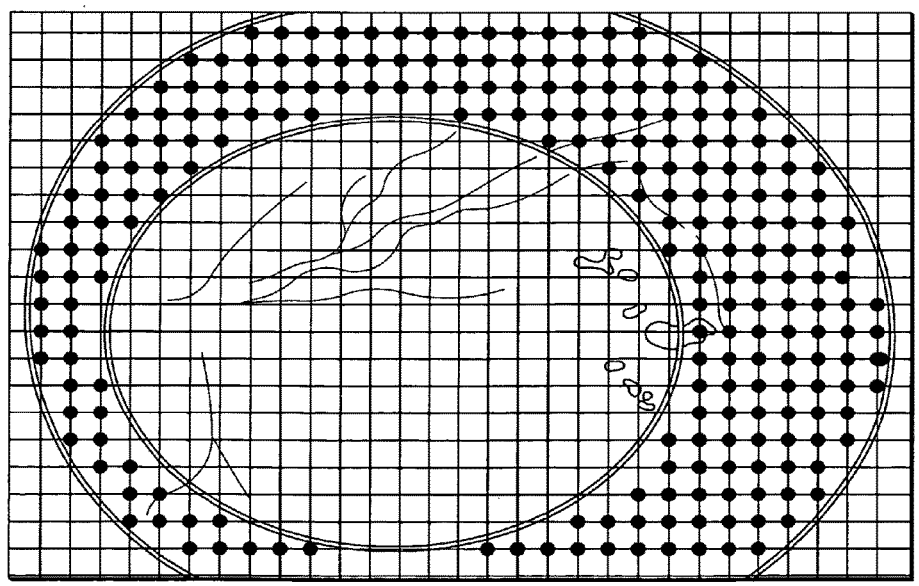
FIG. 10 is an illustration of a human retina, showing a generated grid map on the retina, in accordance with one embodiment of the invention.

According to the invention, the major tasks performed by the local operation module 65 include the following:

(1) acquiring a plurality (preferably, in the range of 5-7) standard fields of the fundus retinal images and transmission of the images to the remote site 58;

(2) receiving the oval area encompassing the focused region of the retina outlined by the remote physician (see FIGS. 5 and 7), as well as parameters for the spot size, power and duration of laser application;

(3) applying a snake algorithm (i.e. active contour algorithm) to extract the contours, calculating the corresponding areas between the contours, and partitioning the image into a grid map (see FIG. 10), as a function of the specified surgical area and corresponding parameters for laser application from the remote center. According to the invention, the resolution of the grid is adjusted according to the area between the contours, whereby the number of nodes between the contours (i.e. the black points between the two white contours) is large enough to generate in the range of approximately 700-1000 laser spots to ensure the surgery precision;

(4) performing the scatter laser coagulation under the remote doctor's command. During the process (which is performed in real-time), the Kalman filter and mean shift algorithm are preferably integrated to detect and estimate the test subject's eye movement: a) if the movement is under the given safety threshold, the laser system will be adjusted using a simple proportional-integral-derivative (PID) control algorithm based on the estimated motion so that it will be focused on the remotely specified spot within allowable surgical accuracy, and then the laser will be applied; b) if the estimated movement is beyond the specified safety threshold, the laser coagulation procedure will be terminated immediately and a warning message will be transmitted to the remote control module 64. Step (1), above, will also be repeated until a stop instruction is received from the remote physician; and (5) acquiring a plurality (preferably, in the range of 4-5) standard fields of fundus retinal images and transmitting the images to the remote site for evaluation and verification of treatment.

Local Operation and Performance Simulation Module

According to the invention, the local operation and performance simulation module 67 allows the physician (or technician) to test the entire system 50 (e.g., tracking and interruption functions in the local operation module 65; communications between local and remote sites; safety and verification modules 66, 72 at both remote and local sites) before the system 50 is run in an actual control mode.

In the simulation mode, the local simulation module 67 replaces the test subject (or patient), but all the other modules (e.g., modules at the remote site 70, 72, 74; safety and verification module 66 and local operation module 65 at the local site) preferably operate in exactly the same manner.

In one or more embodiments of the invention, the local operation and performance simulation module 67 is configured to test the tracking functions of the local operation module 65 by replacing the test subject with a digitized fundus image of him or her. The tracking system is tested using the digitized fundus image in place of the test subject by displacing the digitized fundus image in the X, Y, and O directions (see FIG. 9). The displacement of the digitized fundus image simulates the head and/or eye movement of the test subject that is experienced in the actual control mode. The laser is activated in the simulation mode, but is configured to turn off if the movement of the digitized fundus image exceeds a certain predetermined threshold so as to simulate the actual movement of the test subject exceeding a predetermined threshold.

Any rapid displacement beyond a certain predetermined threshold value or range of values (e.g., an orientation change exceeding 3-5 degrees) cannot be immediately compensated for by the tracking system. As a result, in such a situation, the local operation and performance simulation module 67 is configured to simulate the response of the tracking system to the detection of a displacement exceeding the threshold value or range by shutting down the laser of the laser coagulation system. In the simulation mode, the digitized fundus image can be slightly tilted or laterally displaced (e.g., moving the image on the screen of a visual display device or mechanically, by displacing the screen itself containing the image with a multi-dimensional actuator) to simulate the deactivation of the laser. In some embodiments, the tracking system is configured to follow a particular spot on the fundus image. When the spot being followed by the tracking system is rapidly tilted or displaced, the laser is shut down by the laser coagulation system. This simulated test is used to ensure that the tracking system is fully operational and functioning properly prior to the performance of the laser surgery (i.e., in the actual control mode).

While performing the simulation using a digitized fundus image of the eye is preferred, a physical model of an eye can also be used to perform the simulation carried out by the local operation and performance simulation module 67. For example, an artificial eye can be placed in front of the lens of the laser-imaging apparatus. In such an artificial eye, the retina of the eye is visible through the pupil thereof. In this configuration, the tracking system of the laser coagulation system is tested by slightly displacing the artificial eye in front of the lens of the laser-imaging apparatus (e.g., by using mechanical means, such as a multi-dimensional mechanical actuator) while the laser is activated, but is not firing any actual laser shots. When the detected displacement exceeds the threshold value or range, the tracking system is triggered so as to shut down the laser.

Remote Operations Module

According to the invention, the remote operation module 70 provides the physician with an interface to a personal computer. During a laser procedure, some of the important tasks that the physician will perform and are facilitated by the remote operation module) include: (1) screening via digitized photos, (2) outlining an oval area encompassing the center part of the retina (see FIGS. 5 and 7), (3) choosing the spot size and duration of laser application, (4) adjusting the power via single shots of test spots (preferably, with a duration in the range of approximately 0.001-0.1 seconds in approximately 0.06 intervals), (5) executing virtual treatment with the simulation module (see FIG. 6), (6) performing a test surgery, which involves the local operation and performance simulation module 67, and (7) performing the laser surgery in the actual control mode (and observing the surgery via a real-time video stream).

In one or more embodiments of the invention, the remote operation module 70 further comprises an electronic visual display device with touchscreen capabilities, which is operatively coupled to a personal computer or another digital appliance that has processing capabilities (e.g., a portable digital device, such as a mobile phone or smartphone, a laptop computing device, a palmtop computing device, a tablet computing device, etc.) As such, the laser-imaging apparatus (i.e., the fundus camera) is operatively coupled to the visual display device of the remote operation module 70 so that the digitized fundus (retinal) image of the patient is able to be displayed in detail.

The touchscreen system of the remote operation module 70 comprises a display screen that is sensitive to the touch of a finger or a type of stylus (e.g., a pen stylus). The touchscreen-type visual display device includes: (i) touch sensor in the form of a panel with a responsive surface, (ii) a hardware-based controller, and (iii) touchscreen software executed by the personal computer or other digital appliance. The touch sensor employed by the touchscreen may comprise resistive-type sensor(s), capacitive-type sensor(s), or surface acoustic wave sensor(s). Each of these sensor types has an electrical current passing through them, and touching the surface of the screen results in a consequential voltage change. The voltage change is indicative of the location of the touching. The controller is the hardware component that converts the voltage changes produced by the touch sensor into signals that the personal computer or other digital appliance can receive. The touchscreen software instructs the personal computer or other digital appliance as to what is occurring on the touchscreen and on the information delivered from the controller (i.e., what the user is touching and the location of his or her touch) so that the computer or digital appliance can respond accordingly.

Using the touchscreen visual display device, the physician (i.e., the ophthalmologist) can control the laser system with the touch of his or her finger or by using a stylus pen, etc. The visual display device also includes zoom capabilities in order to allow the physician to examine the details of the digitized fundus image (i.e., retinal image) if needed. The display recognizes and interprets the commands of the physician and communicates those commands to the personal computer that controls the laser generation system. As such, the laser generation system is controlled in accordance with the markings made by the physician on the touchscreen. In other words, the laser generation system is configured to carry out the laser treatment in accordance with the indicated markings on the touchscreen. When a typical procedure is being carried out by the physician, the digitized fundus (retinal) image of the patient is initially recalled on the visual display device. Because the fundus image is digitized, the physician is able to precisely sketch/draw on any area of the digitized fundus image so that he or she can indicate the location(s) where the laser pulses should be applied, and as required, the location(s) where the laser pulses should not be applied. For example, the area or areas where the laser pulses are to be applied are shaded and/or denoted using a first predetermined color (e.g., green, which signifies a laser is to be applied thereto), while the area or areas where laser pulses are not to be applied are shaded and/or denoted using a second predetermined color (e.g., red, which signifies that a laser is not to be applied in this region or regions). When the laser coagulation system is operating in either the simulation mode or the actual control mode, any invasion of the area shaded with the second predetermined color (i.e., the red area) will result in the immediate shutting down of the laser. Also, the area(s) where the laser pulses are to be applied can be separated from the rest of the retina by a continuous line of a predetermined color (e.g., a red line) so that there is a clear demarcation on the retinal image. The area or areas that are shaded and/or denoted using the second predetermined color (i.e., red, indicating that laser pulses are not to be applied thereto) may represent a part of the retina containing large retinal vessels, such as the region with the optic nerve head and the fovea, which are sensitive to laser damage and should not be coagulated (e.g., see FIG. 11). The area of the laser coagulation can be contiguous or separated. In general, the distance between each of the laser pulses can vary (e.g., in the range between 0.1 mm and 4.0 mm or between approximately 0.1 mm and approximately 4.0 mm, inclusive). The laser application can be a single pulse as long as it is indicated by a single colored dot (e.g., a green dot), or the quantity of the laser spots can range up to 2500 spots or more. The laser pulse duration can be in the range from one femtosecond to 4.0 seconds, inclusive (or in the range from approximately one femtosecond to approximately 4.0 seconds, inclusive). In other embodiments, the laser pulse duration can exceed 4.0 seconds. The energy level of each pulse can range from 0.01 femtojoule to one joule, inclusive (or between approximately 0.01 femtojoule to approximately one joule, inclusive), and more preferably, between 1 nanojoule to one joule, inclusive (or between approximately 1 nanojoule to approximately one joule, inclusive). The spot size of the laser varies between 0.0001 nanometers (nm) to 2 millimeters (mm), inclusive (or between approximately 0.0001 nm to approximately 2 mm, inclusive).

In addition, in one or more embodiments, the visual display device with touchscreen capabilities displays the degree of energy (e.g., number of laser pulses, laser spot size, laser power or laser energy level) and the number of laser spots applied for a given area. The visual display device also displays all the parameters that are needed or chosen by the operator in addition to the presentation of the virtual image of the test laser application. All of this information is recorded and stored in the computer. The remote laser apparatus, which is located at each of the local sites 51*a*, 51*b*, 51*c* (see FIG. 5), does not perform the laser coagulation if the prior test is not performed. Similarly, after the correction of any parameter of the laser, or any change in the area of application of the laser, a new test application is run to ensure the safety of the procedure.

Also, as a part of the fail safe mechanism of the system, any invasion of the area which is not be subjected to the laser (e.g., the area colored in red by the physician) results in the immediate shutting down of the laser so that the appropriate inspection can be performed and/or corrective actions can be taken. As such, the system has complete control over the area of laser application.

Figure 7:
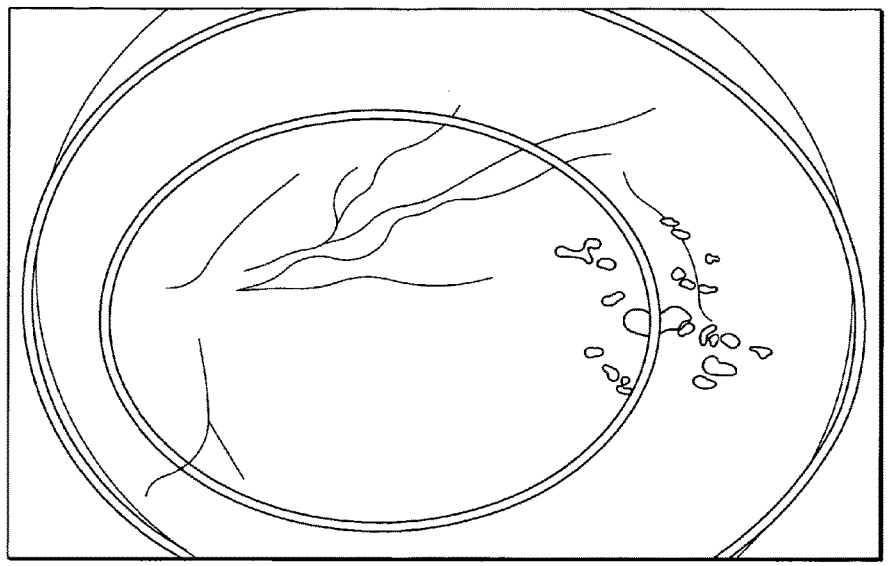
FIG. 7 is an illustration of a human retina, showing an oval area encompassing the target area on the retina for laser transmission, in accordance with one embodiment of the invention.
Figure 8:
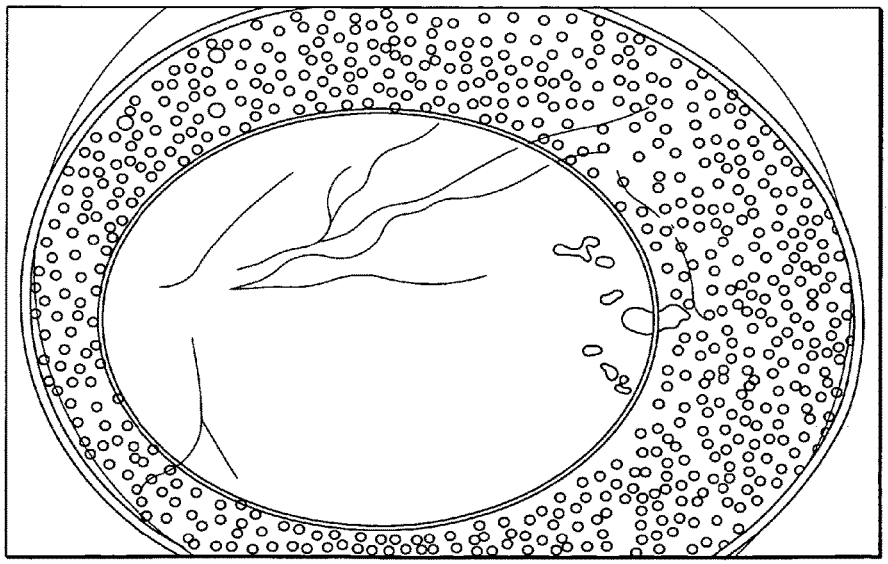
FIG. 8 is an illustration of a human retina, showing the distribution of laser spots resulting from a virtual treatment of the retina, in accordance with one embodiment of the invention.

Referring now to FIGS. 7 and 8, there are shown photographs of the retina, showing the outline of the oval target area (area bound by two oval lines) thereon for application of laser spots (FIG. 7) and the laser spots (in some embodiments, in the range of approximately 50-3000 laser spots) on the retina achieved via virtual treatment (see FIG. 8), as described below. In some embodiments, the physician can draw the oval lines in FIGS. 7 and 8 on the digitized fundus image by utilizing the touchscreen-type visual display device.

Figure 11:
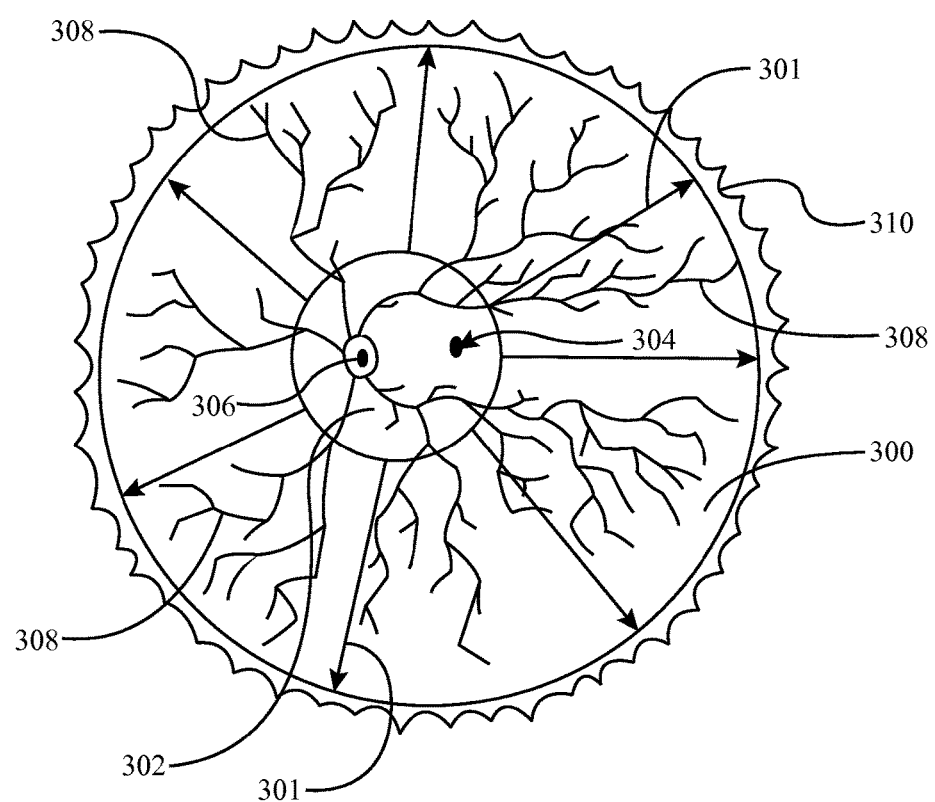
FIG. 11 is an illustration of a human retina, showing a large area of the fundus that is to be coagulated, in accordance with one embodiment of the invention.
Figure 12:
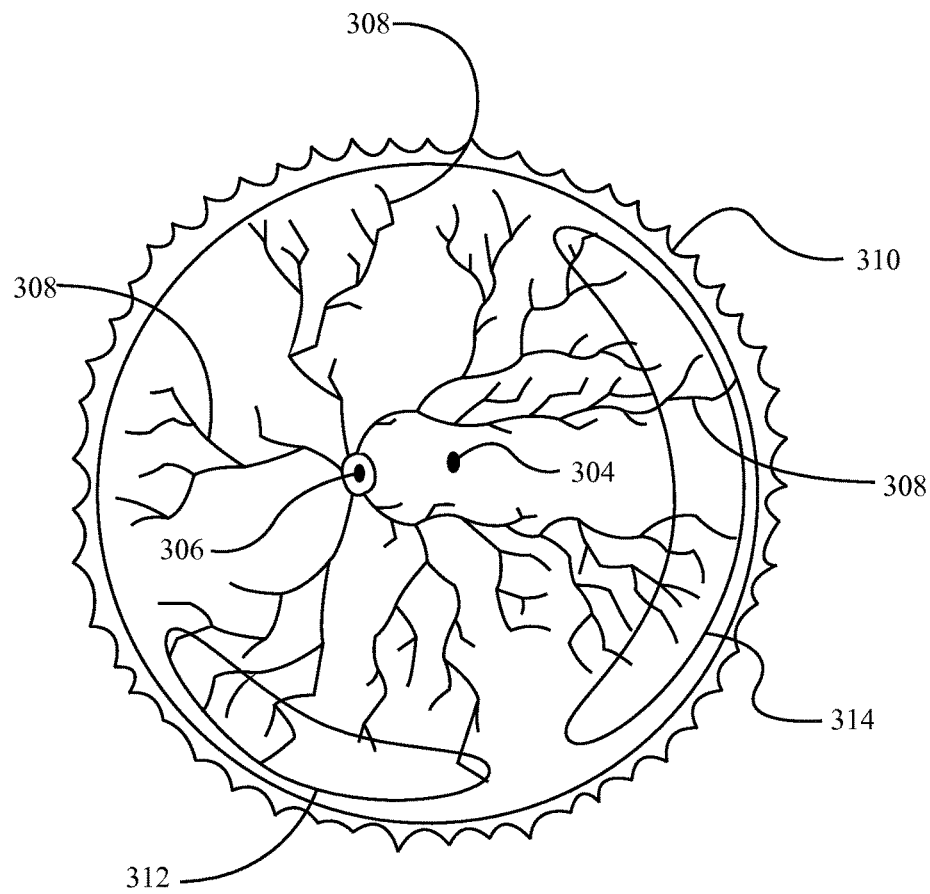
FIG. 12 is an illustration of a human retina, showing localized areas of the fundus that are to be coagulated, in accordance with one embodiment of the invention.
Figure 13:
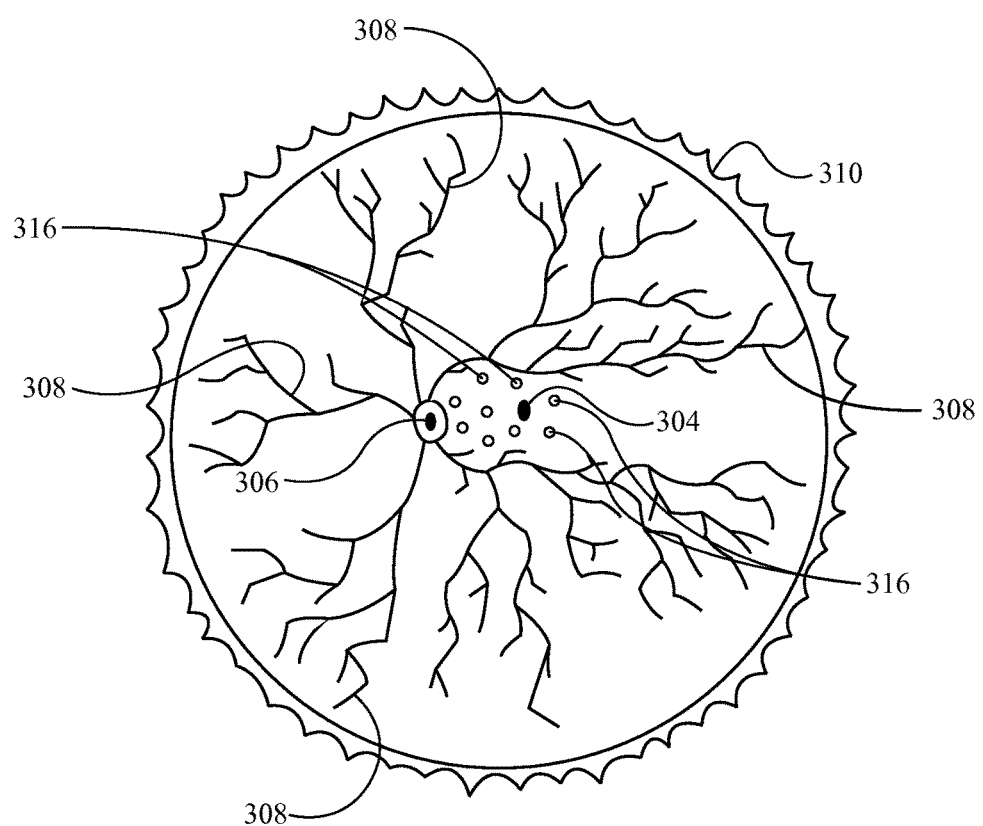
FIG. 13 is an illustration of a human retina, showing single, localized spots of the fundus that are to be coagulated, in accordance with one embodiment of the invention.
Figure 14:
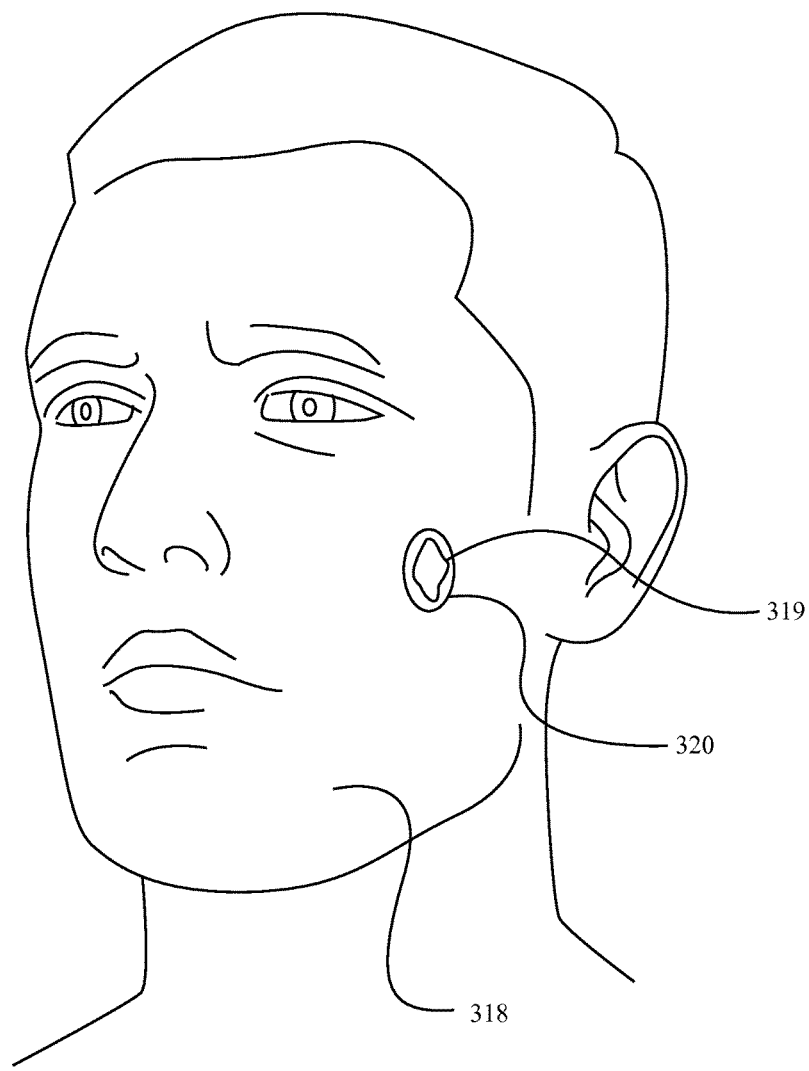
FIG. 14 is an illustration of a human face, showing an area of a skin lesion that is marked for laser application.

Now, turning to FIGS. 11-14, four (4) images showing exemplary areas of laser application on a patient are illustrated (e.g., as marked by a physician using the touchscreen-type visual display device). FIGS. 11-13 depict laser application areas in the retina, which have been indicated on the fundus (retinal) image of a patient, while FIG. 14 depicts a laser application area on the skin surface of a patient. Specifically, in FIG. 11, it can be seen that the annular area 300 (or donut-shaped area 300) with diagrammatic arrows 301 has been marked for laser application (e.g., by using a green color), while the central circular area 302 has been marked for no laser application thereto (e.g., by using a red color). As described above, the fovea 304 and the optic nerve head 306, which are located in the central circular area 302, are highly sensitive to laser damage, and thus, should not be coagulated. As shown in FIG. 11, the retinal area has a plurality of blood vessels 308 disposed throughout; the retinal area is surrounded by the ora serrata 310 (i.e., the serrated junction between the retina and the ciliary body). Next, turning to FIG. 12, two (2) localized areas 312, 314 are marked for laser application (e.g., by using a green color). As shown in FIG. 12, the localized areas 312, 314 are generally elongated, curved regions of the retina. Then, with reference to FIG. 13, it can be seen that a plurality of single localized spots 316 on the retina are marked for laser application (e.g., by using a green color). As illustrated in FIG. 13, the plurality of localized spots 316 are disposed in close proximity to the fovea 304 and the optic nerve head 306.

In addition, it is to be understood that the laser coagulation procedure described herein can also be applied to external surface areas on the body of a patient. For example, in FIG. 14, an area 320 of skin lesion 319 on a patient's face 318 is marked for laser application (e.g., by using a green color). As other examples, the laser coagulation system described herein could be used to treat the eye surface, the cornea, conjunctiva, eyelid, skin areas, or visible mucosa. As such, any part of the eye can be treated with the laser coagulation system described herein using the same laser-imaging apparatus described above, or a modified camera technology that is particularly suited for surface applications (e.g., a standard camera, such as those that are used in photography, or a microscope, etc.). Such a camera would be used to create images of the eye surface, the cornea, conjunctiva, eyelid, skin areas, or visible mucosa, etc.

Remote Operation and Performance Simulation Module

According to the invention, the remote operation and performance simulation module 74 allows a physician or technician to perform virtual treatment, which permits the physician to test the local operation module 65 (at a local site) in terms of its generation capability of the laser spots throughout the surgery area specified by the doctor (see FIG. 8). The algorithm used in this simulation module is similar to the one used by the local operation module 65.

After the physician (i.e., ophthalmologist) outlines the extent of the desired treatment area using the touchscreen visual display device of the remote operation module 70, he or she initiates the simulation process using the remote operation and performance simulation module 74. The treatment area outlined by the physician is filled virtually by the module 74 with dots (e.g., white dots), thereby covering the area and indicating the extent and the density of the laser spots that should occur on the retina and not on any other area.

Figure 9:
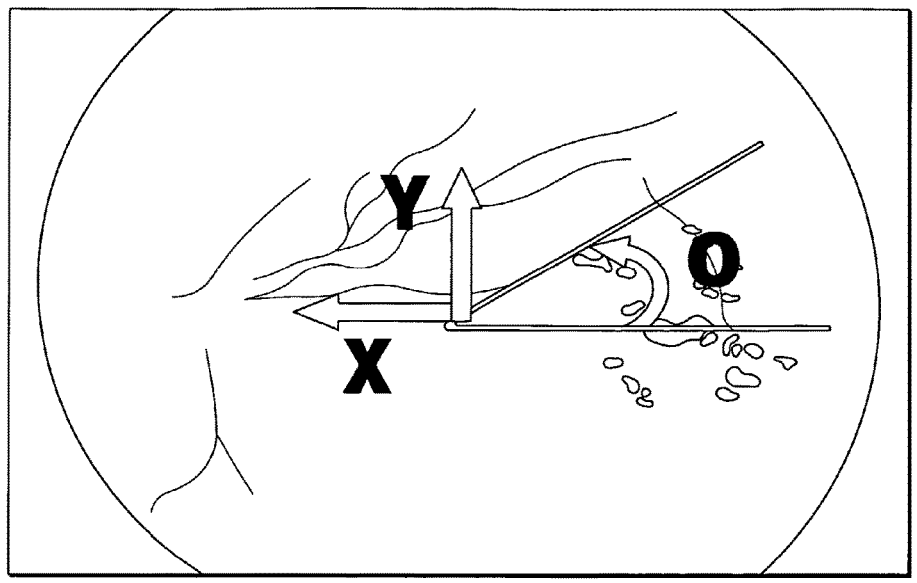
FIG. 9 is an illustration of a human retina, showing simulation variables associated with movement of the eye, in accordance with one embodiment of the invention.

Referring now to FIG. 9, in some embodiments, movement of the object (i.e. digitized fundus photograph) is simulated via three random variables; X, Y and O. The variables X and Y denote the displacement changes in the X and Y axes, respectively. The variable O denotes the orientation changes. In a preferred embodiment, the digitized fundus image is displaced electronically by the remote operation and performance simulation module 74 using the variables X, Y and O. The displacement of the digitized fundus image represents the movement of the retinal image of the patient prior to operating the laser coagulation system in the actual control mode.

In another embodiment, it is also possible to utilize mechanical means to displace a hardcopy of the fundus image (e.g., by using a multi-dimensional mechanical actuator that is operatively coupled to the hardcopy of the fundus photograph).

To this end, movement data from test subjects is first collected, from which best-fit statistical distributions (and variances) for the three random variables (X, Y, and O) are determined. According to the invention, a "goodness-of-fit" test can then be performed to test the validity of the distribution.

If a theoretical distribution (involving larger p-value in statistical sense) exists, it will then be employed. Otherwise, an empirical distribution will be constructed and employed.

According to the invention, the remote operation and performance simulation module 74 also allows the physician to test the local operation module 67 (at a local site) in terms of its generation capability of the laser spots without involving communications with the local control module 62.

Safety and Verification Modules

According to the invention, safety and verification modules 66, 72 exist both at the remote site 58 as well as each local site 52, 54, 56 to ensure safe and effective operation of the system 50. In a preferred embodiment of the invention, several constraints are preferably imposed into the system 50 (both hardware and software). In some embodiments, the constraints include (1) physical constraints, (2) logical constraints, and (3) medical constraints.

According to the invention, physical constraints ensure various parameters or values (e.g., therapy beam power) in the laser system 50 are within a permitted range. If any of the values are outside a permitted range, laser firing will be automatically locked and notification of the unacceptable value(s) is transmitted to the physician at the remote site, as well as the technician at the local site.

Logical constraints are employed to ensure that a correct sequence of operational tasks is performed. For example, if a physician at a remote site mistakenly commands 700-1000 laser spots of laser application to the fundus before simulating the laser application in a simulation mode, the system will not execute the command and transmits a warning message to the physician. In a preferred embodiment, Unified Modeling Language (UML) is incorporated into the system software and employed to specify the logical constraints.

The medical constraints involve monitoring of the fundus of the test subject(s) during the actual laser procedure operation. If it is detected that the laser energy effect on the fundus is different from what the physician expected or the laser energy is applied beyond the specified area, laser energy transmission is immediately terminated. Notification of the issue is also transmitted to the physician at the remote site, as well as the physician or technician at the local site.

As indicated above, in some embodiments of the invention, the system 50 also includes eye tracking and facial recognition means to ensure safe operation.

Laser-Imaging System with Image and Voice Recognition Capabilities

Figure 15:
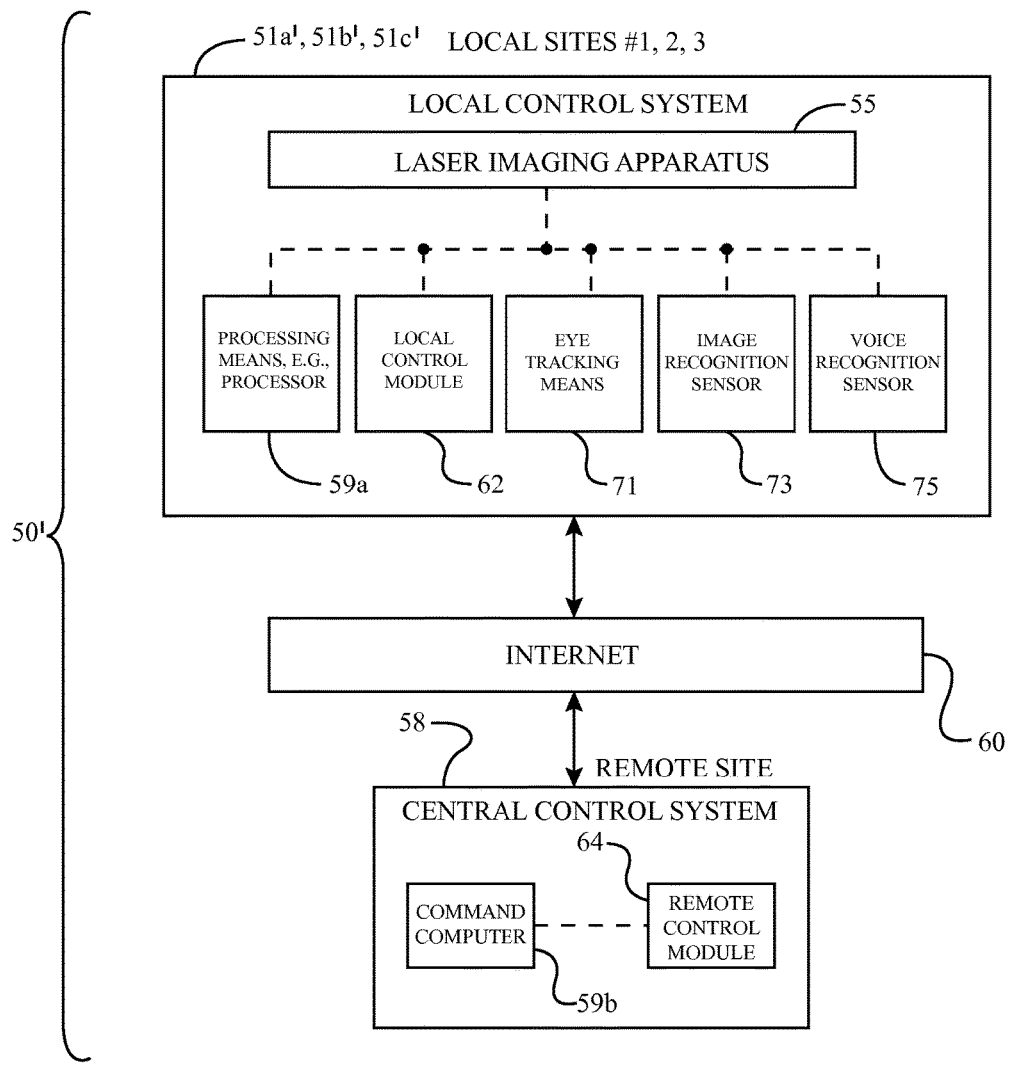
FIG. 15 is a schematic illustration of another embodiment of a laser-imaging system, in accordance with the invention, wherein the local control system of the laser-imaging system comprises image and voice recognition sensors.

Referring now to FIG. 15, there is shown a schematic diagram of a laser-imaging system 50', according to another embodiment of the invention. Referring to this figure, it can be seen that, in many respects, this embodiment of the laser-imaging system 50' is similar to the embodiment of the laser-imaging system 50 described above. Moreover, many elements are common to both such embodiments. For the sake of brevity, the elements that the laser-imaging system 50' has in common with the laser-imaging system 50 will only be briefly mentioned, if at all, because these components have already been explained in detail above. Furthermore, in the interest of clarity, these elements are denoted using the same reference characters that were used in the preceding embodiment.

As illustrated in FIG. 15, like the system 50 described above, the system 50' includes a plurality of local control systems disposed at local sites 51a', 51b', 51c'; each system including a laser-imaging apparatus 55, such as the apparatus 200 shown in FIG. 2. In a preferred embodiment of the invention, each laser-imaging apparatus 55 includes a photoacoustic system, such as system 80 discussed above.

Preferably, each laser-imaging apparatus 55 of the system 50' is preferably in communication with a local control module 62 and control-processing means 59a. In the illustrated embodiment, the control-processing means 59a may be embodied as a local personal computer or local computing device that is specially programmed to carry out all of the functionality that is described herein in conjunction with the local control systems of the laser-imaging system 50'.

In the illustrated embodiment of FIG. 15, each local control system also includes eye tracking means 71 for measuring eye position(s) and movement. According to the invention, the eye tracking means 71 can be an integral component or feature of the laser-imaging apparatus 55 or a separate system or device.

Referring again to FIG. 15, it can be seen that each local control system also includes an image recognition sensor 73 for capturing images of a subject or patient that may be used to identify and/or verify the identity of the subject or patient. Advantageously, the positive identification and verification of the identity of the subject or patient receiving treatment prevents surgical mistakes wherein the wrong subject or patient is treated. In addition, rather than identifying and/or verifying the identity of the subject or patient, the image recognition capabilities of the image recognition sensor 73 may also be used to identify and verify that a particular surgical procedure is being performed on the proper body portion of a subject or patient (e.g., to verify that a laser coagulation procedure is being performed on the proper one of the patient's eye or that a surgical procedure is being performed on the proper one of the patient's limbs). In one or more embodiments, the image recognition sensor 73 may comprise a multispectral camera that captures multispectral digital images over a wide range of frequencies of the electromagnetic spectrum (e.g., from visible light frequencies to infrared radiation frequencies). As such, because the camera is capable of operating using a wide range of different frequencies, the multispectral camera may be used as both a visible light camera (e.g., operating in the 450-750 nanometer range) and a thermographic camera for capturing images using infrared radiation (e.g., operating with wavelengths up to 14,000 nm (14 μm)).

In one or more embodiments, the image recognition sensor 73 of each local control system may be operatively connected to the local computing device, which forms the control-processing means 59a of the local control system. The local computing device may be specially programmed with image/pattern recognition software loaded thereon, and executed thereby for performing all of the functionality necessary to identify and verify a particular subject or patient, or to identify and verify a body portion of the particular subject or patient that is to be treated. Initially, the local computing device may be specially programmed to capture and store a first reference digital image of a body portion of the subject or patient so that the first reference digital image may be compared to a second digital image of the same body portion captured at a later time (i.e., just prior to the performance of the surgical procedure). Then, prior to the performance of the surgical procedure (e.g., a laser coagulation performed on the eye), the second digital image of the same body portion of the subject or patient is captured by the image sensor 73 (i.e., the multispectral camera) and the local computing device compares the second digital image of the body portion to the first reference digital image and determines if the second digital image of the body portion matches or substantially matches the first reference digital image. When the local computing device determines that the second digital image of the body portion of the subject or patient matches or substantially matches the first reference digital image, the local computing device is specially programmed to generate a matched image confirmation notification that is sent to the remote computing device at the remote site in order to inform the attending physician that the proper patient or body portion of the patient has been identified and verified. The matched image confirmation notification may also be delivered to the technician at the local site via the local computing device. Then, after the other safety checks of the system 50' have been performed, the surgical procedure is capable of being performed on the patient. Conversely, when the local computing device determines that the second digital image of the body portion of the subject or patient does not match or substantially match the first reference digital image, the local computing device is specially programmed to generate a non-matching image notification that is sent to the remote computing device at the remote site in order to inform the attending physician that the patient or body portion of the patient has not been properly identified and verified. The non-matching image notification may also be delivered to the technician at the local site via the local computing device. When the non-matching image notification is sent to the attending physician, the local computing device also disables the surgical equipment at the local site in order to prevent the procedure from being performed on the incorrect patient or the incorrect body portion of the patient (e.g., in a laser coagulation procedure, laser firing will be automatically locked out by the local computing device).

When the multispectral camera comprising the image recognition sensor 73 is used as a thermographic camera in the mid-infrared or infrared radiation wavelength range, the camera may be used to capture images of capillaries in the skin of the patient or subject. As such, the camera may sense the heat generated by the blood in these capillaries to identify the subject or patient, or a particular body portion of the subject or patient. A multispectral camera that is capable of both visible light photography and infrared pattern recognition takes into account psychological functions which are not achievable with a camera having only visible light capabilities (e.g., two or three different physiological functions of the patient may be taken into account with a multispectral camera). For example, prior to capturing the infrared image of a face of the subject or patient, the subject or patient may be instructed to frown so that wrinkles are made prominent in the face of the subject or patient. When the subject or patient frowns, skin capillaries become collapsed and folded, thereby reducing the blood flow through the collapsed and folded capillaries and the heat that is detected by the multispectral camera. As such, the local computing device may be specially programmed in the manner described above to verify the identity of the subject or patient using the image pattern created by this particular facial expression (i.e., frowning). Detectable wrinkles may also be created by instructing the patient to lift up his or her brow, by instructing the patient to laugh, or by instructing the patient to execute any other facial expression that creates wrinkles. As another example, the multispectral camera may be used to capture a body portion of the subject or patient (e.g., a portion of the patient's skin) that has previously undergone a surgical procedure whereby the structure of the body portion has been altered (e.g., the capillaries in a portion of the patient's skin that has been previously operated on will have a very unique pattern that is specific to the particular patient being verified). The scars created by the surgery create a very different, unique marker on the patient (e.g., scar tissue created by surgery does not have many capillaries). Because this specific pattern of skin capillaries that were surgically altered is extremely hard to artificially replicate, this means of verifying a patient's identity is very reliable and imposters are highly unlikely.

Figure 16:
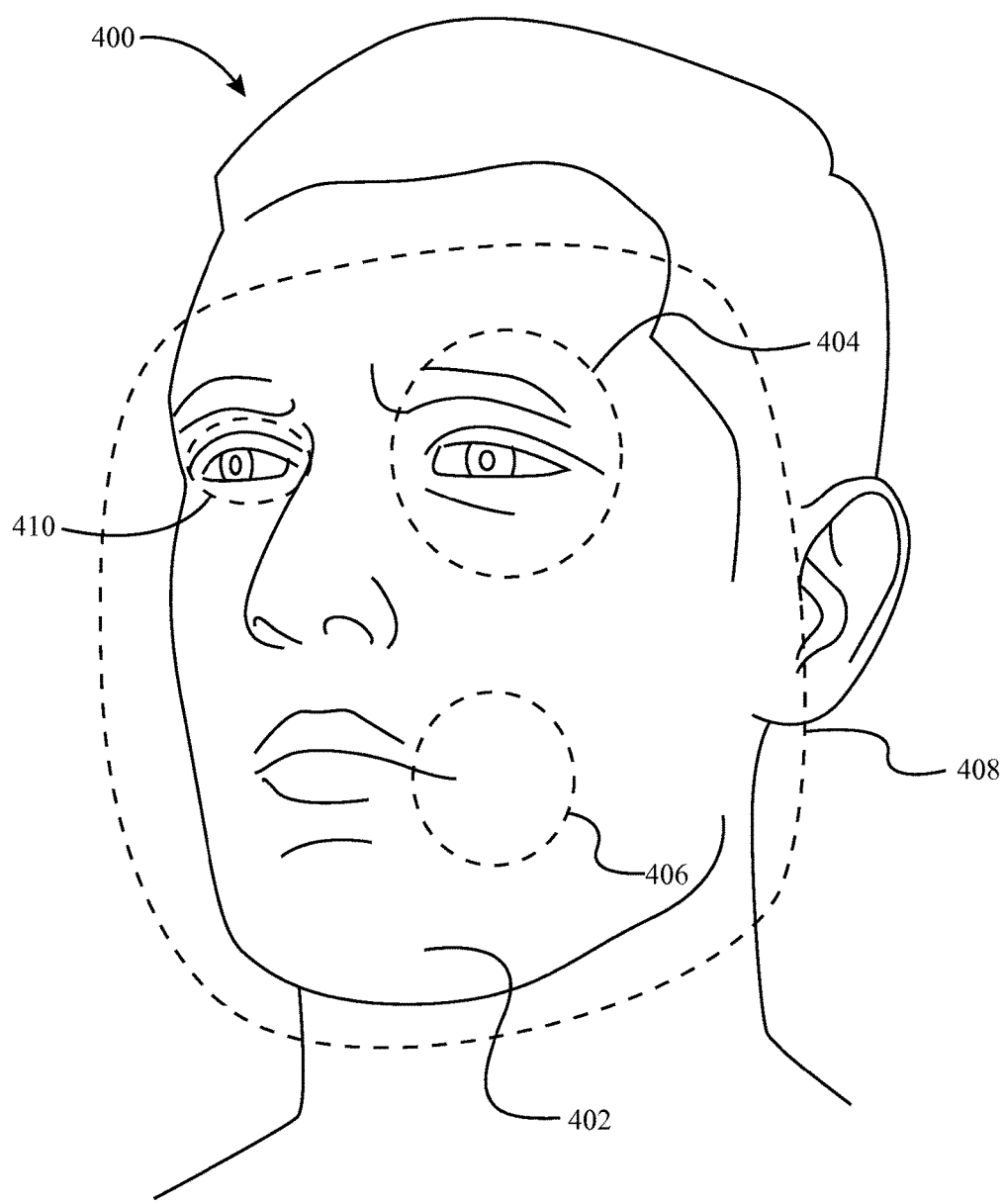
FIG. 16 is an illustration of a human face, showing exemplary areas of the human face that may be imaged so that the identity of a patient or the identity of a body portion of a patient may be verified.

Now, turning to FIG. 16, exemplary image capture areas on a face 402 of a patient 400 are shown. These are merely illustrative examples of some areas that may be imaged by the image recognition sensor 73 of the local control system. The first image capture area 404 in FIG. 16 is disposed around the left eye of the patient 400, and includes the left eye plus the area surrounding the left eye (e.g., so that facial features, such as wrinkles around the eye, may be used for patient identification and verification purposes in addition to the eye itself). The second image capture area 406 in FIG. 16 is disposed around the left corner of the mouth of the patient 400, and includes a portion of the mouth and the area proximate to the mouth (e.g., so that facial features, such as wrinkles around the mouth, may be used for patient identification and verification purposes). The third image capture area 408 in FIG. 16 is disposed around the entire face 402 of the patient 400 (e.g., so that a plurality of different facial features, such as wrinkles disposed throughout the face, may be used for patient identification and verification purposes). When the image of the face 402 of the patient 400 is captured by the image recognition sensor 73, the wrinkles in the face 402 remain dark. It is very difficult to circumvent the image recognition system by replicating wrinkles. The fourth image capture area 410 in FIG. 16 is disposed around the right eye of the patient 400 (e.g., so that the various structures of the right eye, such as the iris and retina, may be used for patient identification and verification purposes).

In addition to the face 402 of the patient 400, it is to be understood that other body surfaces may be imaged by the image recognition sensor 73 of the local control system as well. For example, any portion of the patient's body where the physician would like to apply a laser lesion under observation may be imaged by the image recognition sensor 73. Laser applications may vary from a nearly invisible laser lesion response from the tissue to an obvious burn of a given size or for tissue ablation and evaporation using any suitable laser, such as a gas laser, a solid-state laser, an ultraviolet laser, an infrared laser (i.e., a mid-infrared laser up to a $CO_2$ laser for surface tumor removal or for rejuvenation for cosmetic surgery), an excimer laser (i.e., for corneal surgery) with wavelengths of approximately 192 nm, and a $CO_2$ laser with wavelengths of approximately 10,000 nm (10 micron). Other suitable excimer lasers with various wavelengths may also be used (i.e., excimer lasers with other ultraviolet wavelengths). In addition, microwave or radiofrequency radiation may be applied to the patient from an appropriate unit to achieve the desired therapeutic result. The beam diameter may be varied or be focused to a diameter of one micron to five millimeters or more. The duration of each pulse can vary from one femtosecond to a continuous laser application depending on the need of the operator to achieve a particular result.

Turning again to FIG. 15, it can be seen that each local control system may further include a voice recognition sensor 75 for capturing the speech waveforms generated by the subject or patient so that the speech of the subject or patient may additionally be used to identify and/or verify the identity of the subject or patient. In one or more embodiments, the voice recognition sensor 75 may be used in conjunction with the image recognition sensor 73 described above to further verify that a surgical procedure is being performed on the correct subject or patient. In one or more embodiments, the voice recognition sensor 75 may comprise a microphone that captures the speech of the subject or patient over the entire speech frequency range of a human being (e.g., for a frequency range from 50 Hz to 5,000 Hz to encompass the typical frequency range for both males and females). As such, the syntax and sound pulses generated by the subject or patient are capable of being used by the local control system for verification and identification of the subject or patient prior to the surgical procedure being performed on him or her. In one or more embodiments, the voice recognition sensor 75 may be used as a second means of patient identity confirmation in order to confirm the identity of the patient that was previously verified by the image recognition sensor 73. In other words, the image recognition sensor 73 may comprises a first stage of patient identity confirmation, and the voice recognition sensor 75 may comprise a second stage of patient identity confirmation.

Similar to the image recognition sensor 73 described above, the voice recognition sensor 75 of each illustrative local control system may be operatively connected to the local computing device, which forms the control-processing means 59a of the local control system. The local computing device may be specially programmed with voice recognition software loaded thereon, and executed thereby for performing all of the functionality necessary to identify and verify a particular subject or patient that is to be treated. Initially, the local computing device may be specially programmed to capture and store a first reference speech waveform of the subject or patient so that the first reference speech waveform may be compared to a second speech waveform of the same patient or subject captured at a later time (i.e., just prior to the performance of the surgical procedure). That is, the patient or subject may be asked to say a particular word or plurality words that are captured by the voice recognition sensor 75 so that it can be used as the first reference speech waveform. Then, prior to the performance of the surgical procedure (e.g., a laser coagulation performed on the eye), the second speech waveform of the subject or patient is captured by the voice sensor 75 (i.e., the microphone records the same word or plurality words repeated by the subject or patient) and the local computing device compares the second speech waveform of the patient or subject to the first reference speech waveform and determines if the second speech waveform of the subject or patient matches or substantially matches the first reference speech waveform (i.e., by comparing the frequency content of the first and second speech waveforms). When the local computing device determines that the second speech waveform of the subject or patient matches or substantially matches the first reference speech waveform, the local computing device is specially programmed to generate a matched speech confirmation notification that is sent to the remote computing device at the remote site in order to inform the attending physician that the proper patient has been identified and verified. The matched speech confirmation notification may also be delivered to the technician at the local site via the local computing device. Then, after the other safety checks of the system 50' have been performed, the surgical procedure is capable of being performed on the patient. Conversely, when the local computing device determines that the second speech waveform of the subject or patient does not match or substantially match the first reference speech waveform, the local computing device is specially programmed to generate a non-matching speech notification that is sent to the remote computing device at the remote site in order to inform the attending physician that the patient has not been properly identified and verified. The non-matching speech notification may also be delivered to the technician at the local site via the local computing device. When the non-matching speech notification is sent to the attending physician, the local computing device also disables the surgical equipment at the local site in order to prevent the procedure from being performed on the incorrect patient (e.g., in a laser coagulation procedure, laser firing will be automatically locked out by the local computing device).

Similar to that described above for the system 50 of FIG. 5, the laser-imaging system 50' of FIG. 15 also includes a central control system 58 at a remote site having a command computer 59b that is operatively connected to a remote control module 64. Also disposed at the remote site 58 during a laser procedure is a system operator (e.g., retinal surgeon). In FIG. 15, it can be seen that the central control system 58 at the remote site, which includes the command computer 59b, is operatively connected to the plurality of local control systems disposed at local sites 51a', 51b', 51c' via a computer network that uses the Internet 60.

System Software Platform

The software system that is employed to control the laser procedure(s) with the laser-imaging systems of the invention includes client/server architecture and a TCP/IP communication protocol. The client/server architecture comprises a computer science paradigm, where clients and servers are deemed separate software processes that can run on the same or different computers.

In some embodiments, the software recognizes the computer at the surgeon's site as a client, while the local control module at the remote patient's site is recognized as a server.

According to the invention, communication by and between the remote control module 64 and the local control module 62 is facilitated via web services implemented in .NET remoting technology.

When a physician at a remote site sends a control or data acquisition command, the command is first transmitted to the local control module 62 (or server) through the .NET remoting interface. In response to the command, the local control module 62 controls hardware compartments through a hardware specific interface (e.g., RS-232C interface, parallel communication protocol).

The communication speed between the client and the server will depend on several factors such as 1) the distances between the client and the server, 2) network traffic conditions, and 3) the size of data (e.g., images) being transmitted.

As will readily be appreciated by one having ordinary skill in the art, the present invention provides numerous advantages compared to prior art methods and systems for laser coagulation procedures. Among the advantages are the following:

The provision of laser-imaging systems, which will significantly reduce laser transmission and, hence, procedure time. For example, the length of time for the laser photo-coagulation treatment for diabetic retinopathy will be reduced from 30-60 minutes per procedure to only two minutes. In general, the duration of a single laser pulse, plus the time it takes to perform the subsequent laser application multiplied by the total number of pulses required is equal to the overall procedure time. The manner in which the pulses are applied in a conventional contact system (e.g., using a contact lens positioned on the cornea in order to see the fundus) requires the physician (i.e., ophthalmologist) to perform the procedure laser shot by laser shot (i.e., to place a single laser spot at a desired location and then move on to the next location). When performing the procedure on a patient that requires 1000-2000 laser spots, the laser coagulation procedure can easily take 30 minutes or more. The laser coagulation system disclosed herein uses millisecond laser pulses (and in some cases, less than millisecond pulses), and each subsequent laser shot is performed automatically, in some embodiments, by utilizing an oscillating mirror (e.g., oscillating mirror 220 described above) placed in the path of the laser beam such that the laser beam is displaced without requiring any manual means. In addition, the wide angle camera employed in one or more embodiments described herein enables the entire retina to be viewed, rather than just a small portion thereof, thereby further reducing procedure time. As a result of these enhanced features, the laser coagulation system described herein substantially reduces the overall procedure time. In one embodiment, the remote operation module of the laser coagulation system is configured to perform a fully automated and continuous laser coagulation procedure over the entire area of the retina in a period of time no greater than approximately 2 minutes (or no greater than 2 minutes) in an actual control mode.

The provision of laser-imaging systems, which will also reduce the probability of error associated with manual surgery (tremors and misjudgments) via a more precise computerized control mechanism, with additional fail-safe features, and a wider angle imaging camera for retina diseases. This offers more choices for various lasers with different wavelengths, intensities, and action than was previously possible.

The provision of laser-imaging systems, which will also allow a physician or surgeon to perform a procedure at a remote site, via a high-speed reliable Internet® connection, thus eliminating the need for the patient to travel a long distance to be treated at a specialist's office or, in the case of military field care or space exploration units, allowing patients to be treated immediately on-site.

The laser coagulation system described herein is in the form of a non-contact system that does not require the use of a contact lens or any other device in contact with the eye of the patient. The laser coagulation system embodied herein also does not require the physician to indent any portion of the patient's eye (i.e., no indenter or scleral depressor is required to indent the peripheral portion of the patient's eye). As a result, the patient is far more comfortable during the laser coagulation procedure.

The cameras employed in the systems can also be equipped with appropriate diode lasers and filters for auto-fluorescence photography and angiography of the retina.

One can also develop a miniature version of the system by using printing technology, such as inkjet, to generate and integrate the micro-optical parts not only on hard substrates, but also on those that are flexible. Having a miniature or micro-system will allow further use of such technology in hard to reach places.

Any of the features or attributes of the above described embodiments and variations can be used in combination with any of the other features and attributes of the above described embodiments and variations as desired.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A system for laser coagulation of an eye structure or a body surface, comprising:
    a local control system disposed at a first location and a central control system disposed at a remote site, said remote site being at a second location, said local control system being operatively coupled to said central control system by means of a computer network;
    at least a first laser-imaging system disposed at said first location, said laser-imaging system including a laser-imaging apparatus, a laser generation system, a first computing device with a first processor, and a local control module;
    said laser-imaging apparatus including a digital image acquisition system configured to acquire digitized images of said eye structure or said body surface of a patient, said local control module including local operation, local operation and performance simulation, and local safety and verification sub-modules, said local operation sub-module configured to acquire said digitized images of said eye structure or said body surface from said digital image acquisition system and transmit said digitized images to said remote site, said local operation and performance simulation sub-module configured to test said system prior to its operation in an actual control mode by using one of said digitized images of said eye structure or said body surface of said patient in a simulation mode;
    said laser generation system including an aiming laser configured to generate and transmit an aiming laser beam to said eye structure or said body surface, and a treatment laser configured to generate and transmit at least a first coagulation laser beam to said eye structure or said body surface;
    said central control system including a second computing device with a second processor, and a remote control module, said remote control module including remote operation, remote operation and performance simulation, and remote safety and verification sub-modules;
    said remote operation sub-module being configured to facilitate communications between a remote physician and said second processor of said second computing device, and said remote operation sub-module configured to initiate said simulation mode carried out by said local operation and performance simulation sub-module so as to execute a virtual treatment of said eye structure or said body surface and perform a laser coagulation procedure on said eye structure or said body surface in said actual control mode in which said treatment laser is configured to transmit said first coagulation laser beam to said eye structure or said body surface so as to surgically alter said eye structure or said body surface; and
    said first laser-imaging system further including an image recognition sensor operatively coupled to said first computing device, said image recognition sensor being in the form of a multispectral camera configured to capture multispectral images of said patient using both visible light and infrared light that are produced as a result of said patient being instructed to perform a task that alters one or more detectable physical attributes of said patient, said image recognition sensor configured to capture said multispectral images of said patient at said first location so that an identity of said patient or an identity of a body portion of said patient is capable of being identified and verified prior to said laser coagulation procedure being performed on said eye structure or said body surface in said actual control mode, said first computing device being specially programmed to utilize said multispectral images so as to collectively take into account at least one physiological function and a plurality of physiological characteristics of a body area of said patient that reflect said one or more altered physical attributes when said identity of said patient or said identity of said body portion of said patient is identified and verified, said plurality of physiological characteristics of said body area of said patient including at least two of the following: (i) a blood flow pattern in a body region of said patient, (ii) surface structures of a skin portion of said patient, and (iii) scar tissue in a body region of said patient, and said body area of said patient including at least one of the following: (i) an eye of said patient and skin surrounding said eye of said patient that contains wrinkles, (ii) a portion of a mouth of said patient and skin surrounding said mouth of said patient that contains wrinkles, and (iii) a skin region of said patient that contains scar tissue, said first computing device being further specially programmed to compare a first reference digital image of said patient reflecting said one or more altered physical attributes and said at least one physiological function captured by said image recognition sensor at a first time to a second digital image of said patient reflecting said one or more altered physical attributes and said at least one physiological function captured by said image recognition sensor at a second subsequent time, and to determine if said second digital image of said patient substantially matches said first reference digital image of said patient.

2. The laser coagulation system according to claim 1, wherein said treatment laser of said laser generation system is configured to transmit laser energy in the form of a plurality of pulses having a pulse duration in the range between approximately one femtosecond and approximately four seconds, inclusive.

3. The laser coagulation system according to claim 2, wherein the energy level of each of said plurality of pulses emitted by said treatment laser of said laser generation system is in the range between approximately 0.01 femtojoule to approximately one joule, inclusive.

4. The laser coagulation system according to claim 1, wherein said digital image acquisition system comprises a wide angle digital image acquisition system, said wide angle digital image acquisition system including at least one retinal viewing camera that provides a field of view of said retina in a range between approximately 160° and approximately 200°.

5. The laser coagulation system according to claim 4, wherein said wide angle digital image acquisition system comprises a concave mirror.

6. The laser coagulation system according to claim 1, wherein said system for laser coagulation of an eye structure or a body surface is in the form of a non-contact system that does not require contact with said eye structure or said body surface.

7. The laser coagulation system according to claim 1, wherein, when said first computing device determines that said second digital image of said patient substantially matches said first reference digital image of said patient, said first computing device is specially programmed to generate a matched image confirmation notification that is sent to said second computing device at said remote site in order to inform said remote physician that said patient has been identified and verified; and
when said first computing device determines that said second digital image of said patient does not substantially match said first reference digital image of said patient, said first computing device is specially programmed to generate a non-matching image notification that is sent to said second computing device at said remote site in order to inform said remote physician that said patient has not been properly identified and verified.

8. The laser coagulation system according to claim 7, wherein, when said first computing device determines that said second digital image of said patient does not substantially match said first reference digital image of said patient, said first computing device is further specially programmed to automatically lock out said treatment laser so that said treatment laser is not capable of being fired.

9. The laser coagulation system according to claim 7, wherein, when said first computing device determines that said second digital image of said patient substantially matches said first reference digital image of said patient, said first computing device is further configured to deliver said matched image confirmation notification to a technician at said first location; and
when said first computing device determines that said second digital image of said patient does not substantially match said first reference digital image of said patient, said first computing device is further configured to deliver said non-matching image notification to said technician at said first location.

10. The laser coagulation system according to claim 1, wherein said first laser-imaging system further includes a voice recognition sensor configured to capture speech waveforms generated by said patient at said first location so that an identity of said patient is capable of being identified and verified prior to said laser coagulation procedure being performed on said eye structure or said body surface in said actual control mode.

11. The laser coagulation system according to claim 10, wherein said voice recognition sensor is operatively coupled to said first computing device, said first computing device being specially programmed to compare a first reference speech waveform of said patient captured by said voice recognition sensor at a first time to a second speech waveform of said patient captured by said voice recognition sensor at a second subsequent time, and to determine if said second speech waveform of said patient substantially matches said first reference speech waveform of said patient.

12. The laser coagulation system according to claim 11, wherein, when said first computing device determines that said second speech waveform of said patient substantially matches said first reference speech waveform of said patient, said first computing device is specially programmed to generate a matched speech confirmation notification that is sent to said second computing device at said remote site in order to inform said remote physician that said patient has been identified and verified; and
when said first computing device determines that said second speech waveform of said patient does not substantially match said first reference speech waveform of said patient, said first computing device is specially programmed to generate a non-matching speech notification that is sent to said second computing device at said remote site in order to inform said remote physician that said patient has not been properly identified and verified.

13. The laser coagulation system according to claim 12, wherein, when said first computing device determines that said second speech waveform of said patient does not substantially match said first reference speech waveform of said patient, said first computing device is further specially programmed to automatically lock out said treatment laser so that said treatment laser is not capable of being fired.

14. The laser coagulation system according to claim 10, wherein said voice recognition sensor is in the form of a microphone configured to capture said speech waveforms generated by said patient over a speech frequency range between 50 Hertz and 5,000 Hertz.

15. The laser coagulation system according to claim 1, wherein said plurality of physiological characteristics of said body area of said patient that are capable of being collectively taken into account when said identity of said patient or said identity of said body portion of said patient is identified and verified further include at least one of the following: (i) an iris pattern of an eye of said patient, and (ii) a retinal pattern of an eye of said patient.

16. A system for laser coagulation of an eye structure or a body surface, comprising:
a local control system disposed at a first location and a central control system disposed at a remote site, said remote site being at a second location, said local control system being operatively coupled to said central control system by means of a computer network;
at least a first laser-imaging system disposed at said first location, said laser-imaging system including a laser-imaging apparatus, a laser generation system, a photoacoustic system, a first computing device with a first processor, and a local control module;
said laser-imaging apparatus including a digital image acquisition system configured to acquire digitized images of said eye structure or said body surface of a patient, said local control module including local operation, local operation and performance simulation, and local safety and verification sub-modules, said local operation sub-module configured to acquire said digitized images of said eye structure or said body surface from said digital image acquisition system and transmit said digitized images to said remote site, said local operation and performance simulation sub-module configured to test said system prior to its operation in an actual control mode by using one of said digitized images of said eye structure or said body surface of said patient in a simulation mode;
said laser generation system including an aiming laser configured to generate and transmit an aiming laser beam to said eye structure or said body surface, and a treatment laser configured to generate and transmit at least a first coagulation laser beam to said eye structure or said body surface;

said photoacoustic system being operatively coupled to said laser generation system, said photoacoustic system including an ultrasound transducer configured to detect acoustic waves that are generated as a result of the absorption of energy by said eye structure or said body surface such that said photoacoustic system is able to determine a temperature of said eye structure or said body surface subjected to laser energy from said first coagulation laser beam, said photoacoustic system further being configured to control said laser generation system by maintaining said laser energy of said first coagulation laser beam at a predetermined energy level so as to produce a uniform coagulation of said eye structure or said body surface;

said central control system including a second computing device with a second processor, and a remote control module, said remote control module including remote operation, remote operation and performance simulation, and remote safety and verification sub-modules;

said remote operation sub-module being configured to facilitate communications between a remote physician and said second processor of said second computing device, and said remote operation sub-module configured to initiate said simulation mode carried out by said local operation and performance simulation sub-module so as to execute a virtual treatment of said eye structure or said body surface and perform a laser coagulation procedure on said eye structure or said body surface in said actual control mode in which said treatment laser is configured to transmit said first coagulation laser beam to said eye structure or said body surface so as to surgically alter said eye structure or said body surface; and said first laser-imaging system further including an image recognition sensor operatively coupled to said first computing device, said image recognition sensor being in the form of a multispectral camera configured to capture multispectral images of said patient using both visible light and infrared light that are produced as a result of said patient being instructed to perform a task that alters one or more detectable physical attributes of said patient, said image recognition sensor configured to capture said multispectral images of said patient at said first location so that an identity of said patient or an identity of a body portion of said patient is capable of being identified and verified prior to said laser coagulation procedure being performed on said eye structure or said body surface in said actual control mode, said first computing device being specially programmed to utilize said multispectral images so as to collectively take into account at least one physiological function and a plurality of physiological characteristics of a body area of said patient that reflect said one or more altered physical attributes when said identity of said patient or said identity of said body portion of said patient is identified and verified, said plurality of physiological characteristics of said body area of said patient including at least two of the following: (i) a blood flow pattern in a body region of said patient, (ii) surface structures of a skin portion of said patient, and (iii) scar tissue in a body region of said patient, and said body area of said patient including at least one of the following: (i) an eye of said patient and skin surrounding said eye of said patient that contains wrinkles, (ii) a portion of a mouth of said patient and skin surrounding said mouth of said patient that contains wrinkles, and (iii) a skin region of said patient that contains scar tissue, said first computing device being further specially programmed to compare a first reference digital image of said patient reflecting said one or more altered physical attributes and said at least one physiological function captured by said image recognition sensor at a first time to a second digital image of said patient reflecting said one or more altered physical attributes and said at least one physiological function captured by said image recognition sensor at a second subsequent time, and to determine if said second digital image of said patient substantially matches said first reference digital image of said patient.

17. The laser coagulation system according to claim 16, wherein, when said first computing device determines that said second digital image of said patient substantially matches said first reference digital image of said patient, said first computing device is specially programmed to generate a matched image confirmation notification that is sent to said second computing device at said remote site in order to inform said remote physician that said patient has been identified and verified; and when said first computing device determines that said second digital image of said patient does not substantially match said first reference digital image of said patient, said first computing device is specially programmed to generate a non-matching image notification that is sent to said second computing device at said remote site in order to inform said remote physician that said patient has not been properly identified and verified.

18. The laser coagulation system according to claim 17, wherein, when said first computing device determines that said second digital image of said patient substantially matches said first reference digital image of said patient, said first computing device is further configured to deliver said matched image confirmation notification to a technician at said first location; and when said first computing device determines that said second digital image of said patient does not substantially match said first reference digital image of said patient, said first computing device is further configured to deliver said non-matching image notification to said technician at said first location.

19. The laser coagulation system according to claim 17, wherein, when said first computing device determines that said second digital image of said patient does not substantially match said first reference digital image of said patient, said first computing device is further specially programmed to automatically lock out said treatment laser so that said treatment laser is not capable of being fired.

20. The laser coagulation system according to claim 16, wherein said digital image acquisition system comprises a wide angle digital image acquisition system, said wide angle digital image acquisition system including at least one retinal viewing camera that provides a field of view of said retina in a range between approximately 160° and approximately 200°.

* * * * *